(12) United States Patent
Brahmstedt et al.

(10) Patent No.: US 11,607,222 B2
(45) Date of Patent: Mar. 21, 2023

(54) FEEDBACK CONTROLLED ANASTOMOSIS DEVICES

(71) Applicant: Myka Labs, Inc., San Francisco, CA (US)

(72) Inventors: Colin Brahmstedt, Boulder, CO (US); Michael Harrison, San Francisco, CA (US); Daniel J. Laser, San Francisco, CA (US)

(73) Assignee: Myka Labs, Inc., San Francisco, CA (US)

( * ) Notice: Subject to any disclaimer, the term of this patent is extended or adjusted under 35 U.S.C. 154(b) by 0 days.

(21) Appl. No.: 17/838,862

(22) Filed: Jun. 13, 2022

(65) Prior Publication Data
US 2022/0323076 A1 Oct. 13, 2022

Related U.S. Application Data

(63) Continuation of application No. 17/719,254, filed on Apr. 12, 2022.
(Continued)

(51) Int. Cl.
*A61B 17/11* (2006.01)
*A61B 34/00* (2016.01)
(Continued)

(52) U.S. Cl.
CPC .............. *A61B 17/11* (2013.01); *A61B 18/12* (2013.01); *A61B 34/73* (2016.02); *A61F 2/04* (2013.01);
(Continued)

(58) Field of Classification Search
CPC ......... A61B 17/11; A61B 18/12; A61B 34/73; A61B 2017/00022; A61B 2017/00199;
(Continued)

(56) References Cited

U.S. PATENT DOCUMENTS

| 8,623,036 B2 | 1/2014 | Harrison et al. |
| 11,039,838 B2 | 6/2021 | Binmoeller et al. |

(Continued)

OTHER PUBLICATIONS

PCT International Search Report and Written Opinion, PCT Application No. PCT/US2022/024490, dated Jun. 27, 2022, 15 pages.

*Primary Examiner* — Richard G Louis
(74) *Attorney, Agent, or Firm* — Fenwick & West LLP

(57) ABSTRACT

A system and a method are disclosed for forming an anastomosis between a first layer of tissue and a second layer of tissue of a patient's body. The system includes a first anastomosis device component and a second anastomosis device component configured to interact with the first anastomosis device component. The first anastomosis device component is configured to be delivered to a first lumen inside the patient's body. The second anastomosis device component is configured to be delivered to a second lumen inside the patient's body. The second anastomosis device includes one or more sensors configured to capture sensor data for determining an alignment of the second anastomosis device component relative to the first anastomosis device component, or for characterizing the position or orientation of the second anastomosis device component in three-dimensional space.

33 Claims, 21 Drawing Sheets

Related U.S. Application Data

(60) Provisional application No. 63/285,256, filed on Dec. 2, 2021, provisional application No. 63/173,955, filed on Apr. 12, 2021.

(51) Int. Cl.
  *A61F 2/04* (2013.01)
  *A61B 18/12* (2006.01)
  *A61B 17/00* (2006.01)
  *A61B 18/00* (2006.01)

(52) U.S. Cl.
  CPC ............... *A61B 2017/00022* (2013.01); *A61B 2017/00199* (2013.01); *A61B 2017/00292* (2013.01); *A61B 2017/00557* (2013.01); *A61B 2018/00595* (2013.01); *A61F 2002/044* (2013.01)

(58) Field of Classification Search
  CPC ........... A61B 2017/00292; A61B 2017/00557; A61B 2018/00595; A61F 2/04; A61F 2002/044
  See application file for complete search history.

(56) References Cited

U.S. PATENT DOCUMENTS

| | | | |
|---|---|---|---|
| 2002/0042625 A1* | 4/2002 | Stack | A61B 17/11 606/194 |
| 2002/0128672 A1* | 9/2002 | Dinger | A61F 2/064 623/1.36 |
| 2004/0199054 A1* | 10/2004 | Wakefield | A61B 34/73 600/160 |
| 2004/0215214 A1* | 10/2004 | Crews | H01F 41/026 606/139 |
| 2005/0080439 A1 | 4/2005 | Carson et al. | |
| 2006/0150986 A1* | 7/2006 | Roue | A61F 2/04 128/848 |
| 2011/0218476 A1* | 9/2011 | Kraemer | A61M 25/0068 604/8 |
| 2013/0253548 A1* | 9/2013 | Harrison | A61B 17/11 606/153 |
| 2013/0253550 A1* | 9/2013 | Beisel | A61B 17/11 606/153 |
| 2015/0122870 A1 | 5/2015 | Zemlok et al. | |
| 2016/0022266 A1* | 1/2016 | Lukin | A61B 17/1114 606/154 |
| 2017/0265866 A1 | 9/2017 | Ryou et al. | |
| 2018/0360450 A1 | 12/2018 | Shelton, IV et al. | |
| 2019/0000560 A1* | 1/2019 | Berman | A61B 1/0002 |
| 2020/0138438 A1 | 5/2020 | Harrison et al. | |

\* cited by examiner

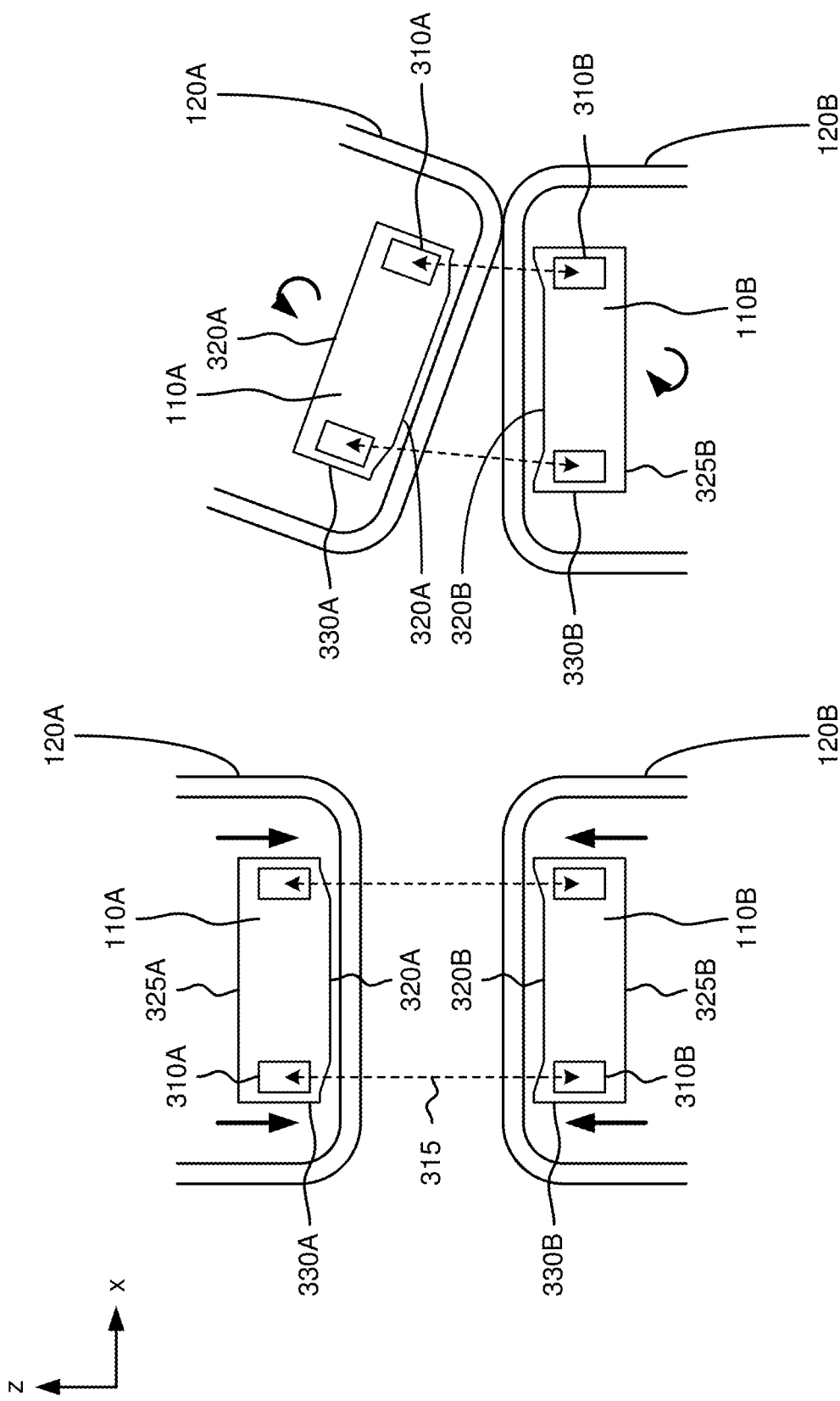

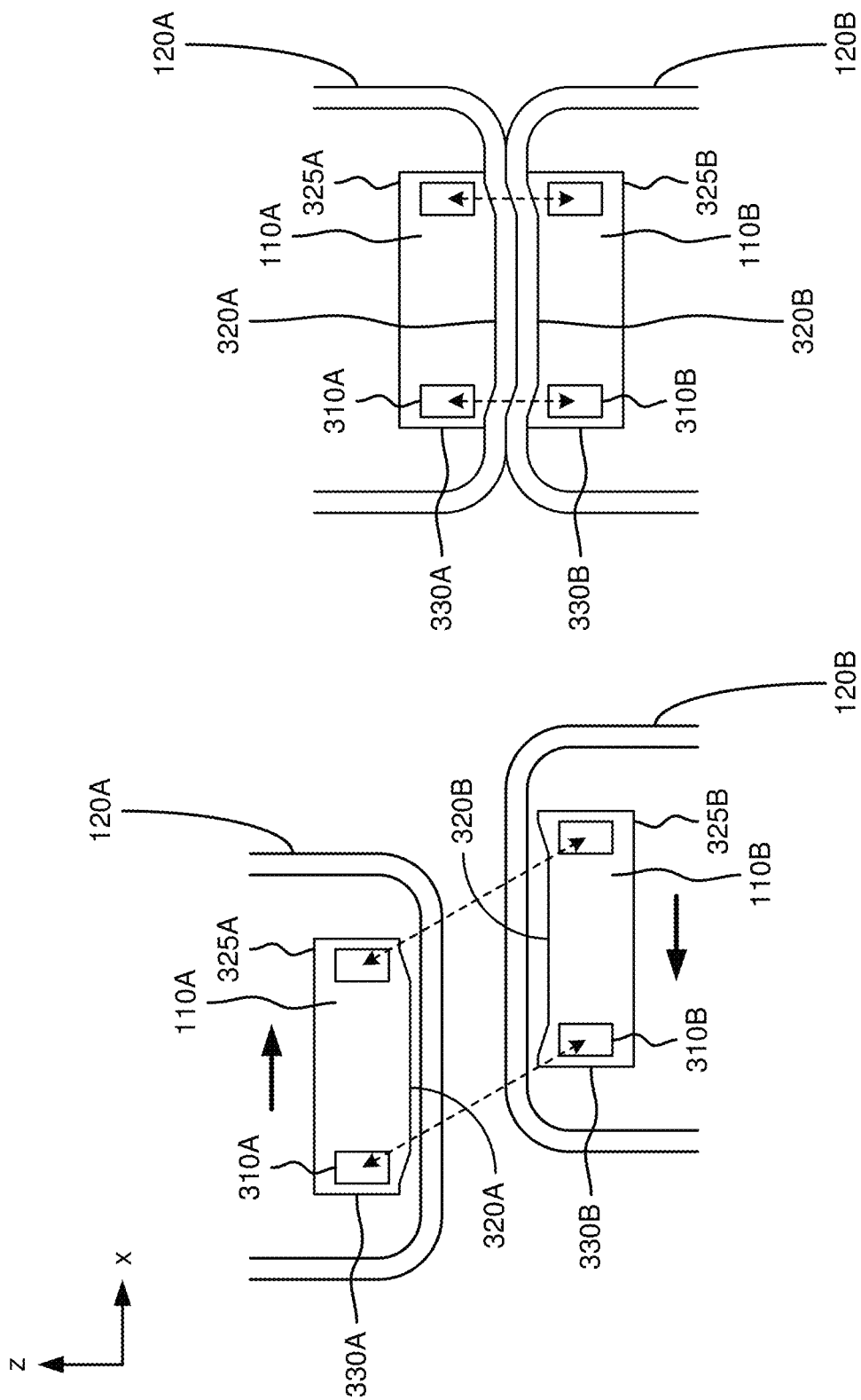

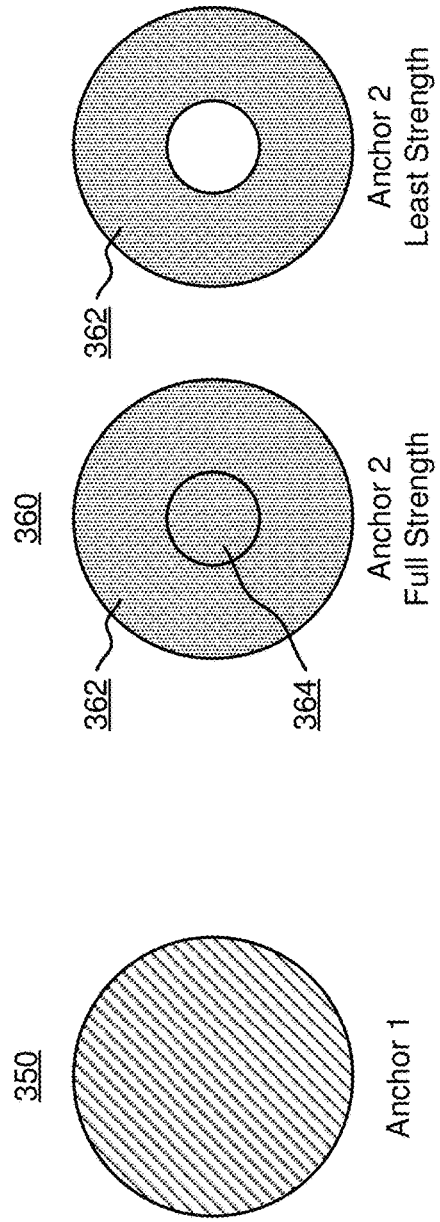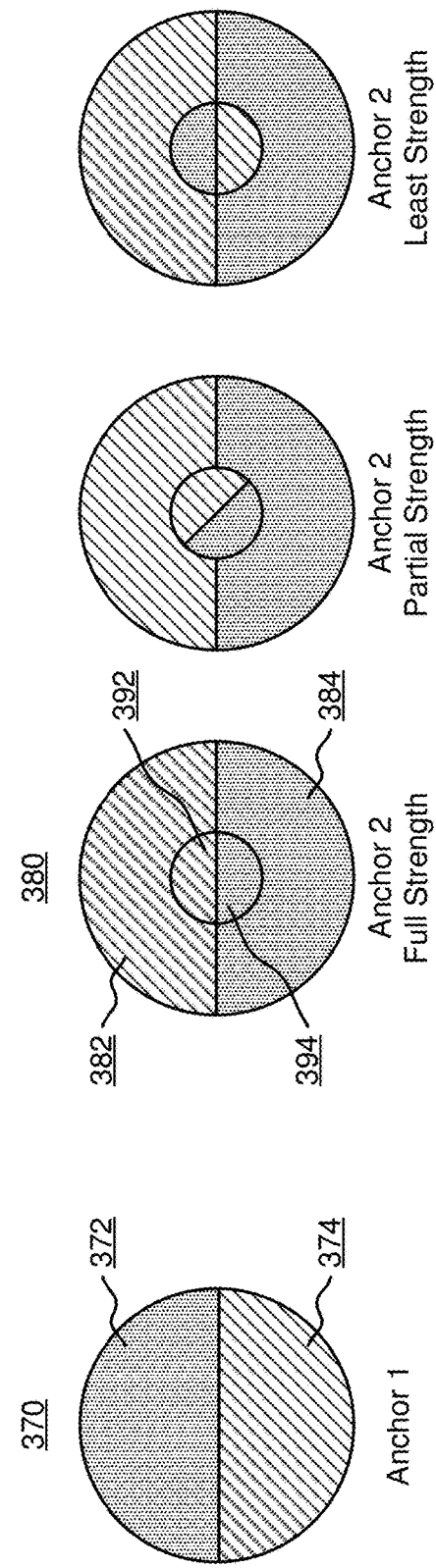
FIG. 3E
FIG. 3F

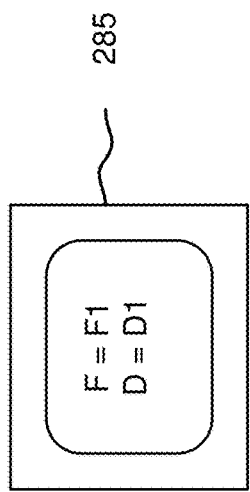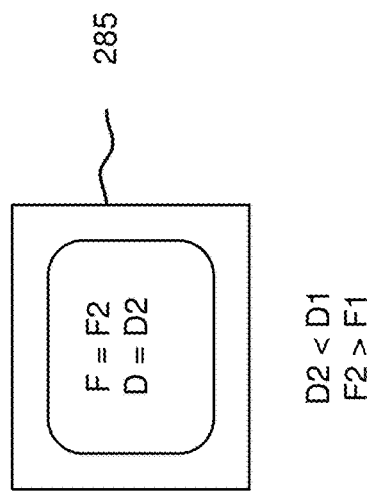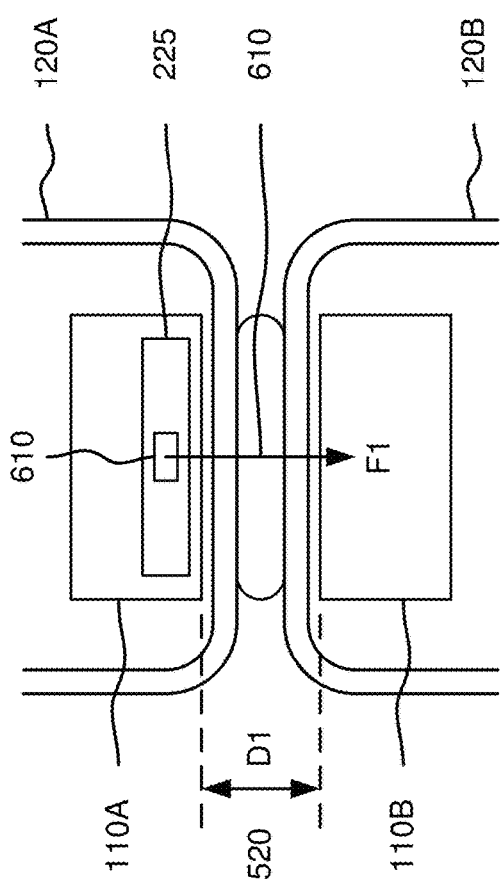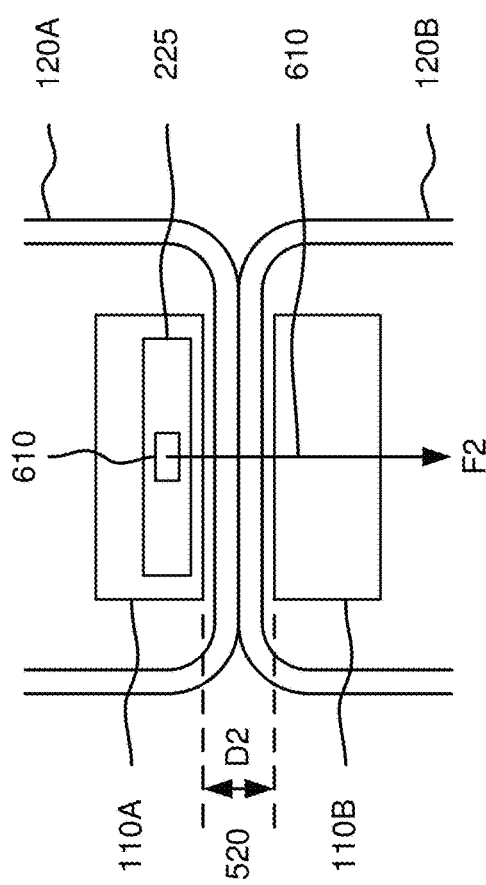

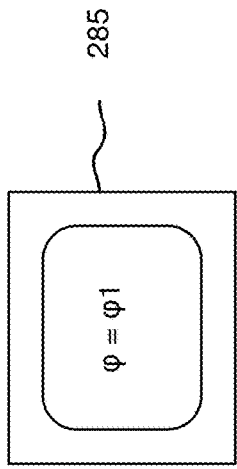
FIG. 7A
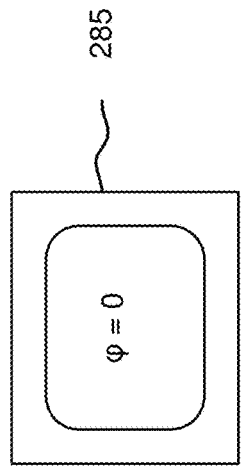
FIG. 7B
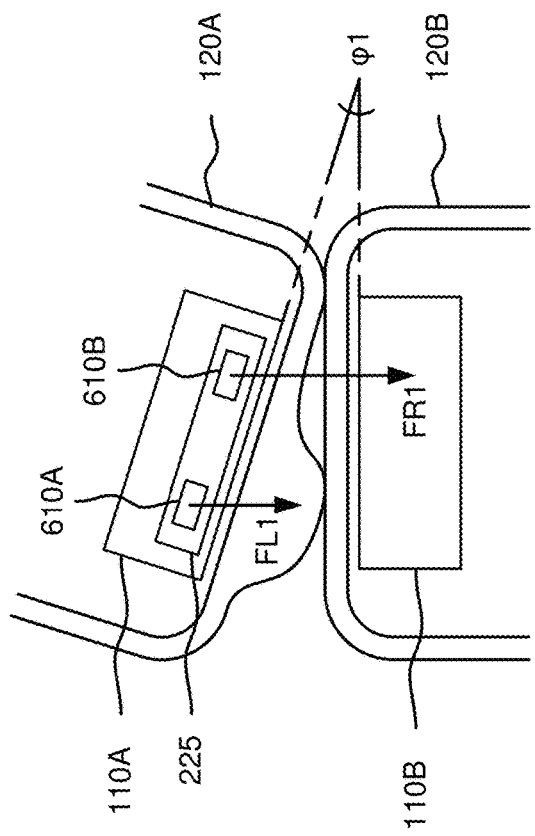

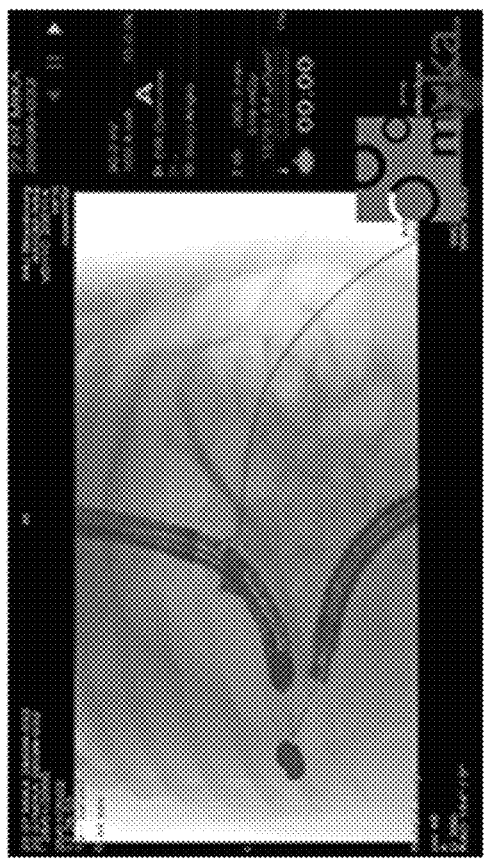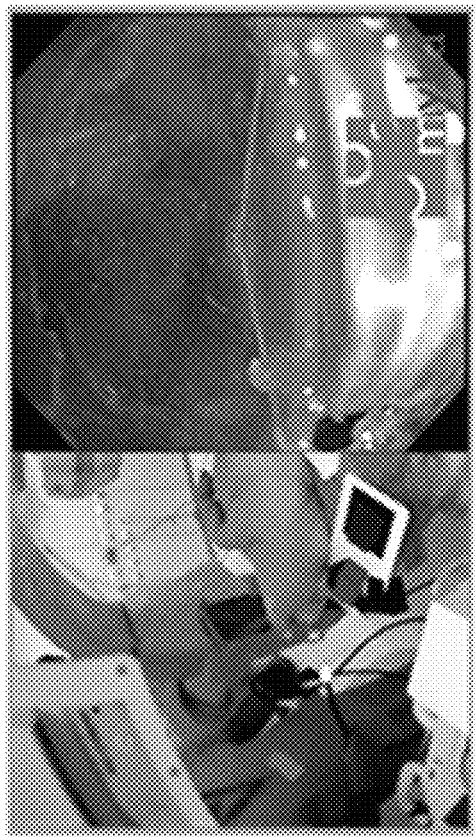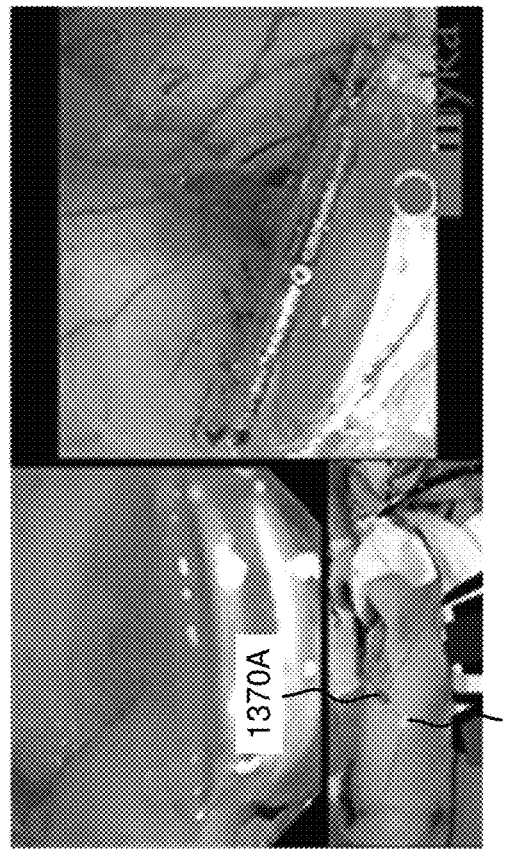
FIG. 13D

FEEDBACK CONTROLLED ANASTOMOSIS DEVICES

CROSS REFERENCE TO RELATED APPLICATIONS

This application is a continuation application of U.S. application Ser. No. 17/719,254, filed on Apr. 12, 2022, which claims the benefit of U.S. Provisional Application No. 63/173,955, filed Apr. 12, 2021, and U.S. Provisional Application No. 63/285,256, filed Dec. 2, 2021, all of which are incorporated by reference in their entirety.

BACKGROUND

An anastomosis is a connection between two lumens in the body through which material can flow. For example, when a cancerous section of the colon is surgically removed, the joining together of the upstream section and the downstream section of the colon to restore continuity (i.e., to re-create a lumen through which material can flow) is referred to as surgically creating an anastomosis. Historically, GI tract anastomoses were created by hand-sewing. Later, a variety of staplers and other specialized device systems were developed to facilitate anastomosis creation. Where specialized device systems are used for anastomosis creation, the devices often comprise at least two components, where a first device component is positioned in a first lumen and a second device component is positioned in a second lumen. A surgeon brings the two device components in such a way that the two device components interact with another and join the lumens.

For example, to create an anastomosis between the stomach and the small bowel in the course of a Roux-en-y bypass, a surgeon may punch the anvil of a circular stapler through the stomach wall and then through a section of small bowel wall. The surgeon will then bring the anvil into the main part of the circular stapler and will then fire the staples.

Creation of an anastomosis between the stomach and the small bowel can also be used for treating pancreatic cancer patients, to bypass obstruction at the outlet of the stomach, a condition known as malignant gastric outlet obstruction (MGOO).

Device systems can be designed with magnetic elements such that magnetic force can be leveraged in bringing two lumens together to create an anastomosis. Device systems with ring- or disk-shaped magnetic elements have been used in the past.

In practice, however, device systems with magnetic elements are not commonly used for anastomosis creation. One reason that magnetic force-based device systems have gained only limited traction for anastomosis creation is that, historically, these device systems have lacked features and functionality to accommodate challenging anatomy. For example, a lump of fibrotic tissue can come to be interposed between two magnetic device components, which can be a problem for anastomosis formation.

This is problematic because it unbalances the magnetic components such that the attraction between the portion of the two device components without the fibrotic tissue interposed between is strong, while the attraction between the portion of the device components where the fibrotic tissue sits in between them is weak. However, in this example, the opposite would often be preferable: the surgeon would like to have more force acting at the portion with the fibrotic tissue interposed between the magnetic components to compress the lump of fibrotic tissue and allow for a better anastomosis. There is limited ability to address this issue, particularly considering that precise characterization of the position and orientation of magnetic device components is needed in order to compress the fibrotic tissue.

SUMMARY

A system and a method are disclosed for forming an anastomosis between a first layer of tissue and a second layer of tissue of a patient's body. The system includes a first anastomosis device component and a second anastomosis device component configured to interact with the first anastomosis device component. The first anastomosis device component is configured to be delivered to a first lumen inside the patient's body. The second anastomosis device component is configured to be delivered to a second lumen inside the patient's body. The second anastomosis device includes one or more sensors configured to capture sensor data for determining an alignment of the second anastomosis device component relative to the first anastomosis device component, or for characterizing the position or orientation of the second anastomosis device component in three-dimensional space.

In some embodiments, the first anastomosis device component includes one or more magnetic elements. Moreover, the second anastomosis device component includes one or more magnetic elements configured to interact with the magnetic elements of the first anastomosis device component through the first layer of tissue and the second layer of tissue of the patient's body.

In other embodiments, the first anastomosis device includes a structured that can be filled with a gas or liquid (e.g., a saline solution). Similarly, the second anastomosis device component includes a structure that can be filled with a gas or liquid. The structure in the first anastomosis device and the structure in the second anastomosis device may be able to enlarge and become rigid upon forcing a gas or liquid into the structures.

In yet other embodiments, the first anastomosis device component includes a mesh or woven structure that can be transitioned between a deployment configuration and a therapeutic configuration. Similarly, the second anastomosis device component includes a mesh or woven structure that can be transitioned between a deployment configuration and a therapeutic configuration. In some embodiments, in the therapeutic configuration, the first anastomosis device component has a flange shape. Moreover, in the therapeutic configuration, the second anastomosis device component has a flange shape and an adjoining cylindrical region.

BRIEF DESCRIPTION OF THE DRAWINGS

The teachings of the embodiments can be readily understood by considering the following detailed description in conjunction with the accompanying drawings.

FIG. 3A illustrates a coupling module of a first anastomosis device component interacting with a second coupling module of a second anastomosis device component, according to one or more embodiments.

FIG. 3B illustrates a pair of anastomosis device components having a longitudinal axial misalignment, according to one or more embodiments.

FIG. 3C illustrates a pair of anastomosis device components having a lateral misalignment, according to one or more embodiments.

FIG. 3D illustrates a first anastomosis device component aligned to a second anastomosis device component, according to one or more embodiments.

FIGS. 3E and 3F illustrate magnetic elements including a first magnetic anchor and a second magnetic anchor that can be controlled to increase or decrease the magnetic force between the first and second magnetic anchors, according to one or more embodiments.

FIG. 6A illustrate a diagram of a pair of anastomosis device components having a first distance, according to one or more embodiments.

FIG. 6B illustrate a diagram of a pair of anastomosis device components having a second distance, according to one or more embodiments.

FIG. 7A illustrate a diagram of a pair of anastomosis device components having an angle φ1, according to one or more embodiments.

FIG. 7B illustrate a diagram of a pair of anastomosis device components parallel to each other, according to one or more embodiments.

FIG. 13D illustrates images captured from experimental studies performed using the anastomosis system with an augmented reality display, according to one or more embodiments.

DETAILED DESCRIPTION OF EMBODIMENTS

The Figures (FIG.) and the following description relate to preferred embodiments by way of illustration only. It should be noted that from the following discussion, alternative embodiments of the structures and methods disclosed herein will be readily recognized as viable alternatives that may be employed without departing from the principles of the embodiments.

Reference will now be made in detail to several embodiments, examples of which are illustrated in the accompanying figures. It is noted that wherever practicable, similar or like reference numbers may be used in the figures and may indicate similar or like functionality. The figures depict embodiments for purposes of illustration only.

Overview

Figure 5B:
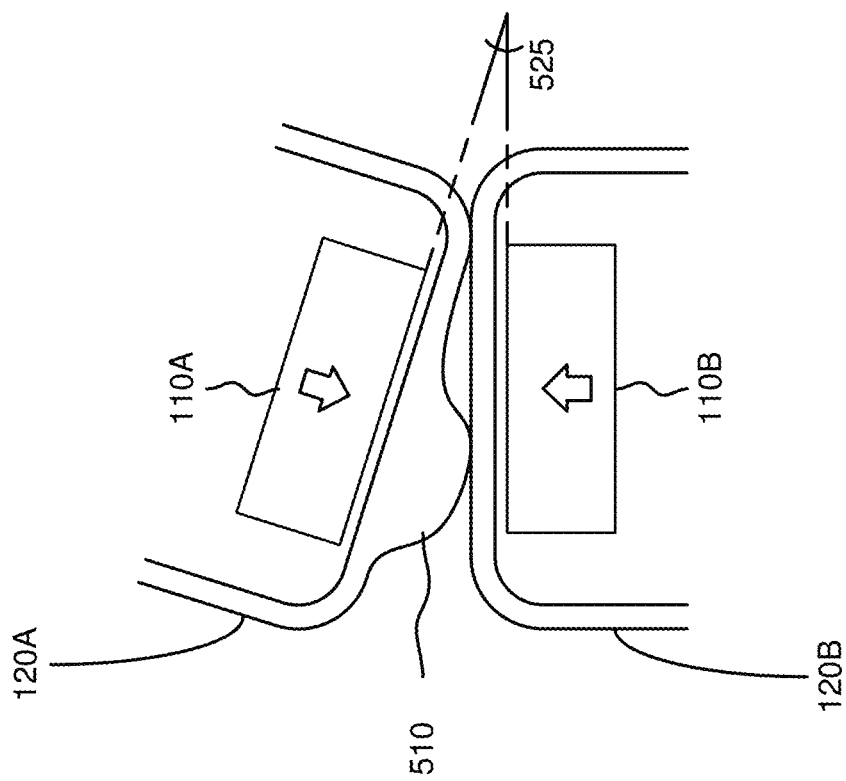
FIGS. 5A and 5B illustrate examples of situations where anatomical features are interposed between the first anastomosis device component and the second anastomosis device component.

Magnetic anastomosis devices (such as those described in U.S. Pat. No. 8,142,454, which is incorporated by reference in its entirety) may be used for connecting areas of tissue, such as two lumens. In practice, however, device systems with magnetic elements are not commonly used for anastomosis creation. One reason that magnetic force-based device systems have gained only limited traction for anastomosis creation is that, historically, these device systems have lacked features and functionality to accommodate certain categories of anatomy that are particularly challenging. For example, as explained above, a lump of fibrotic tissue can come to be interposed between two magnetic device components. This is illustrated in FIG. 5B, where the lump of tissue is shown as element 510. A lump of tissue as depicted here can be problematic because, as FIG. 5B illustrates, the attraction between the right-hand portions of the two device components (110A and B) is comparatively strong, while the attraction between the left-hand portions of the device components (where the lump of tissue is interposed) is comparatively weak. This comparatively weakness and comparative strength is associated with the well-known inverse proportionality of the magnetic force between two elements and the distance between those elements.

Continuing to refer to FIG. 5B, to achieve a desired therapeutic outcome, e.g., anastomosis, it can be preferable to apply a comparatively large force on a region of interposed tissue where at least some of the interposed tissue is fibrotic. Compressing fibrotic tissue can have the effect of bringing about necrosis of fibrotic tissue, which can be favorable from the standpoint of patient outcomes.

Yet, it is difficult to determine that such a lump of fibrotic tissue is interposed between two magnetic components and exactly where this tissue is positioned relative to the two components.

Disclosed is an anastomosis system for connecting areas of tissue, wherein the system includes sensors that provide information about the position and orientation of the device components of the system. Sensors that can be part of the anastomosis devices include gyroscopes, accelerometers, force sensors, and SpO2 sensors. Magnetic elements can be integrated into device components of the system. Sensor information can be fed back to a controller that analyzes the sensor information and produces inputs to actuators in laparoscopic or endoluminal devices. The inputs to the actuators can be chosen to bring about a change in the position or orientation of device components of the system for the purpose of achieving an objective of a medical intervention. For example, the actuators can bring about translation of a device component within a lumen to a position within the lumen that has advantages for creation of an anastomosis, such as an absence of intervening mesentery between the first and second lumens to be joined.

In the embodiments where the position of the anastomosis device is being adjusted by a laparoscopic instrument, the adjustment may take place with an intervening lumen wall. For example, a laparoscopic instrument may be used to apply force to an anastomosis device in such a way as to compress fibrotic tissue interposed between a first anastomosis device and a second anastomosis device. In the embodiments where the position of the anastomosis device is being adjusted by an endoluminal instrument, the adjustment may take place without an intervening lumen wall. For example, an endoluminal instrument can adjust the distribution of discrete magnetic elements within one or both of a pair of anastomosis devices such that compressive magnetic force is of greater magnitude between regions of tissue-contacting surfaces of two anastomosis devices where there is a bulk of intervening fibrotic tissue and of lesser magnitude between regions of tissue-contacting surfaces of two anastomosis devices without a bulk of intervening fibrotic tissue. Many of the examples provided throughout relate to performing a magnetic anastomosis. However, the methods and devices may be applied to any procedure in which areas of tissue are to be connected, as well as to other interventional procedures and diagnostic procedures with devices employing magnetic force, such as for placement of one- or multi-component lumen apposing stents, for longitudinal compression therapy for GI tract strictures and for characterizing the size and stiffness of anatomical features, such as a polyp.

In some embodiments, during a procedure, to provide additional force in the regions where the fibrotic tissue is located, a surgeon (or a surgical robot) may exert force on the left-hand portions, compressing the fibrotic tissue. For example, the tip-bending functionality of an endoscope, or other functionality of an endoscope, can be employed in such exertion of force. Fibrotic tissue can deform largely plastically (as opposed to elastically) such that, after an initial application of force by a surgeon or surgical robot that causes a first stage of fibrotic tissue compression, a force of lesser magnitude can be exerted by or on the anastomosis device components to further compress fibrotic tissue, even when the additional force is removed. Such force of lesser magnitude can be exerted by spring elements, by magnetic elements, or by other elements integrated with or positioned around anastomosis device components.

To address axial misalignment, precise characterization of the position and orientation of anastomosis device components may be useful. Conventional imaging modalities such as fluoroscopy or ultrasound may not have sufficient resolution to create a high-quality anastomosis using magnetic force-based anastomosis devices. Instead, sensors may be embedded in the anastomosis device components to provide information with an improved resolution. The sensor information may be fed back for analysis and used to produce inputs to actuators in laparoscopic or endoluminal devices to bring about a change in the position or orientation of the device components of the anastomosis system.

Although the system is described herein in the context of the creation of an anastomosis, the various components of the system may be used to perform other types of surgery and procedures (See e.g., Appendix below).

System Architecture

Figure 1:
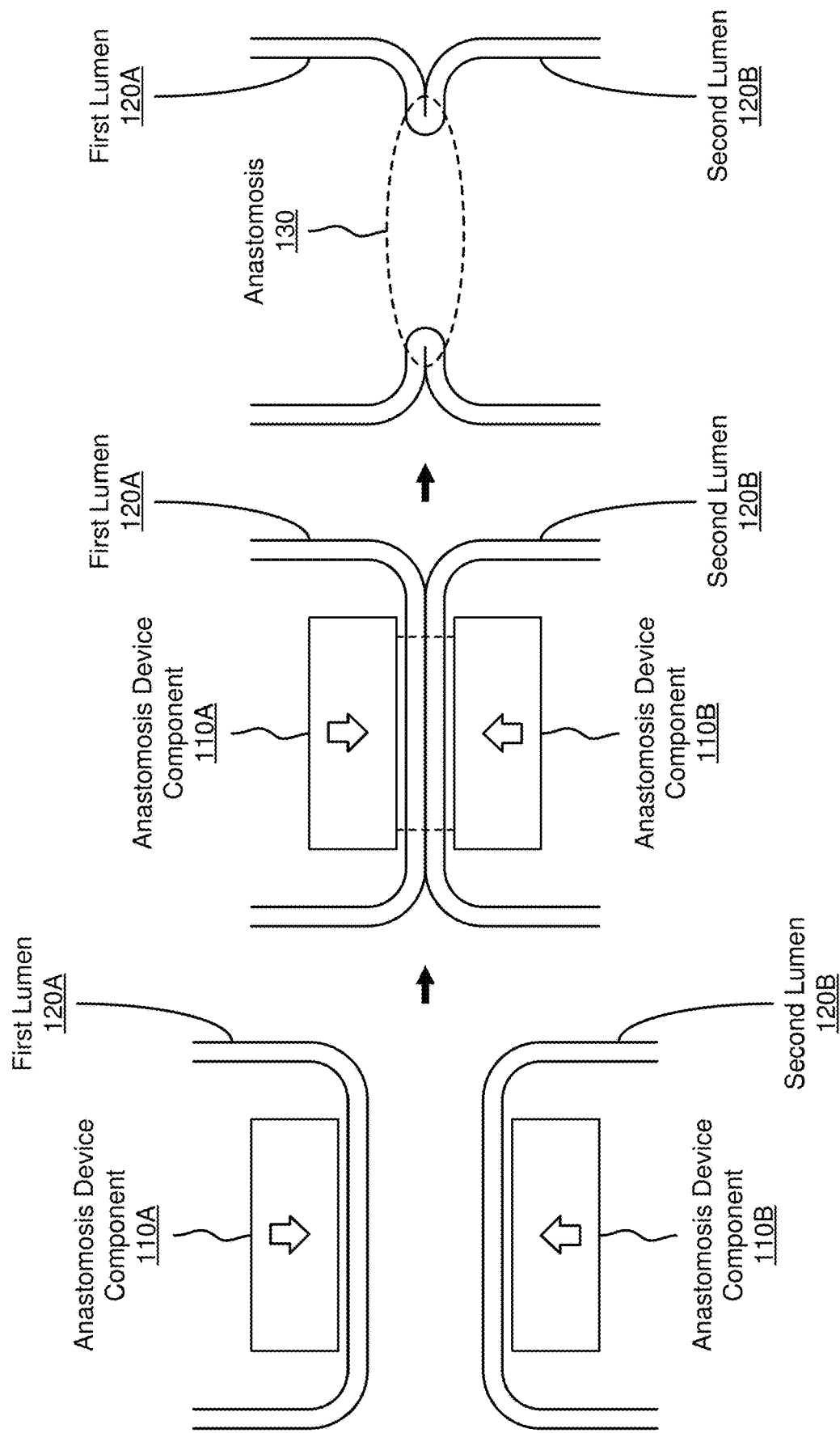
FIG. 1 illustrates two lumens being joined creating an anastomosis between them, in accordance with one or more embodiments.

FIG. 1 illustrates two lumens being joined creating an anastomosis between them, in accordance with one or more embodiments. For example, the two lumens to be joined might be two sections of the small bowel, or the stomach to the small bowel, or the small bowel to the large bowel. To join the first lumen 120A and the second lumen 120B, a first anastomosis device component 110A is placed in the first lumen 120A and a second anastomosis device component 110B is placed in the second lumen 12B. For example, each anastomosis device component 110 may be brought to their respective locations within the small bowel of a patient using catheters designed to carry each of the anastomosis device components 110.

The first anastomosis device component 110A and the second anastomosis device component 110B can be coupled to each other to connect the first lumen 120A and the second lumen 120B to each other. In some embodiments, the first anastomosis device component 110A or the second anastomosis device component 110B includes a tissue modification element to cause a modification (such as a thermal tissue modification, a photothermal tissue modification, or a photoacoustic tissue modification) in the tissue of the outer wall of the first lumen 110A and the outer wall of the second lumen 110B to create a channel or anastomosis 130 cross-connecting the first lumen 110A to the second lumen 110B.

Figure 2:
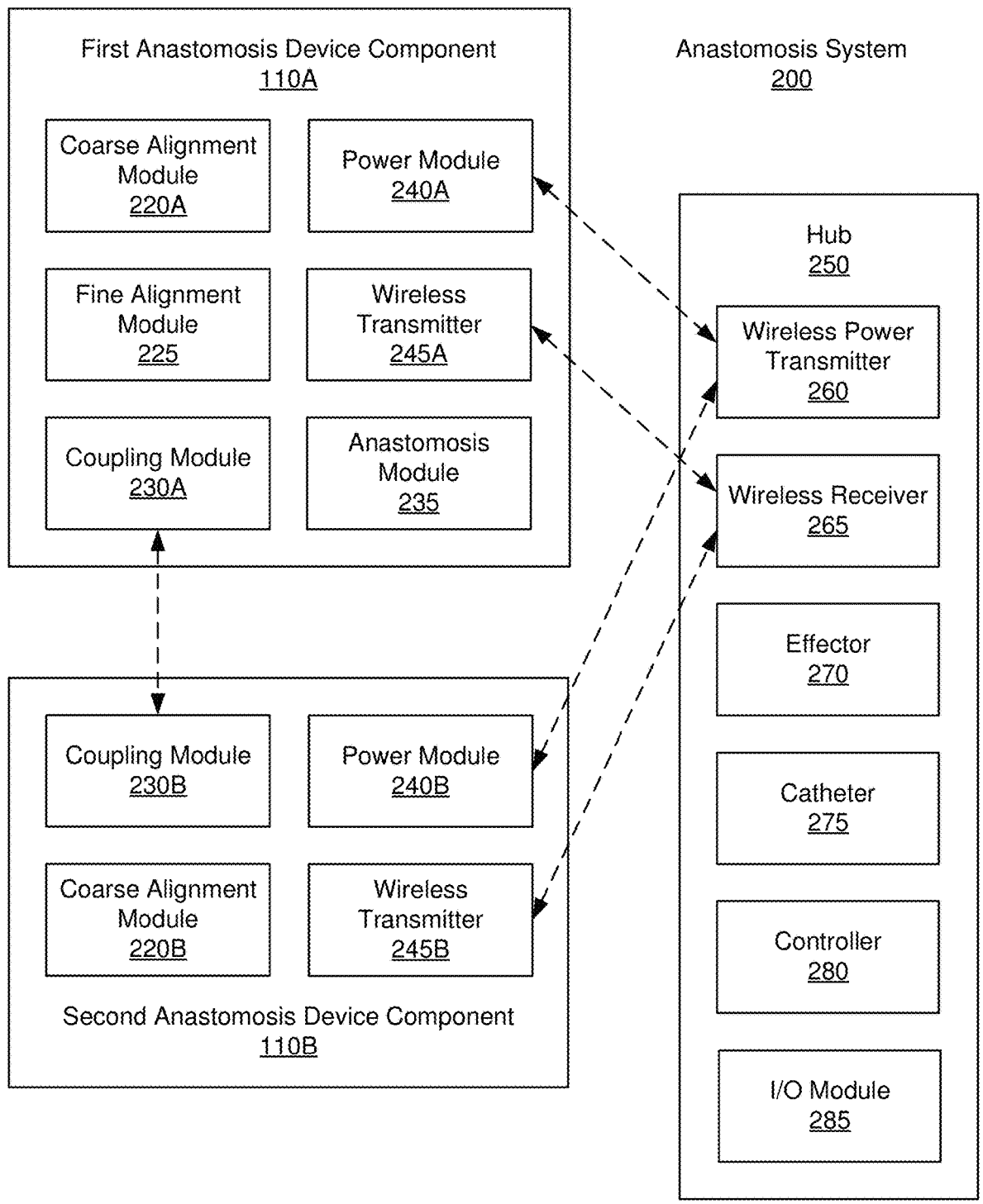
FIG. 2 illustrates a block diagram of an anastomosis system, according to one or more embodiments.

FIG. 2 illustrates a block diagram of an anastomosis system 200, according to one or more embodiments. The anastomosis system 200 includes a first anastomosis device component 110A, a second anastomosis device component 110B, and a hub 250. In some embodiments, the anastomosis system 200 includes additional elements not shown in FIG. 2.

The first anastomosis device component 110A includes a coarse alignment module 220A, a fine alignment module 225, a coupling module 230A, an anastomosis module 235, and a power module 240A. In some embodiments, the second anastomosis device component 110B includes the same components as the first anastomosis device component 110A. In other embodiments, the second anastomosis device component 110B includes less components than the first anastomosis device component 110A. For example, in the embodiment of FIG. 2, the second anastomosis device does not include a fine alignment module 225 or an anastomosis module 235. In yet other embodiments, some of the elements shown as being included in the first anastomosis device component 110A are instead included in the second anastomosis device component 110B. For example, the anastomosis module 235 may be included in the second anastomosis device component 110B instead of the first anastomosis device component 110A.

The coarse alignment module 220 includes sensors for acquiring information as to the position and orientation of the first anastomosis device component 110A, or the second anastomosis device component 110B, or the relative position and orientation of the first and second anastomosis device components 110A and 110B. For example, the coarse alignment module 220 includes sensors such as accelerometers and gyroscopes. In another example, the coarse alignment module 220 may use alternating current electromagnetic tracking.

In another embodiment, the anastomosis device component 110A comprises at least one force sensor that can measure forces acting on the device component 110A, such as forces associated with magnetic field effects between the anastomosis device component 110A and anastomosis device component 110B. In some embodiments, the coarse alignment module 220 includes additional sensors for determining a location of the first anastomosis device component 110A or other instruments or anatomy, e.g., by triangulation or by referencing to one or more known fixed locations outside of the body of the patient.

The fine alignment module 225 includes sensors for determining an alignment between the first anastomosis device component 110A and the second anastomosis device component 110B. For example, the fine alignment module 225 includes sensors that measure forces associated with magnetic field effects, which in turn can yield information about the distance between the first anastomosis device component 110A and the second anastomosis device component 110B. Multiple such sensors can yield information about the relative orientation of the first anastomosis device component 110A and the second anastomosis device component 110B. Additionally, the fine alignment module 225 includes at least one sensor, such as an accelerometer, for determining the absolute orientation of the first anastomosis device component 110A relative to an external frame of reference. In some embodiments, the fine alignment module 225 includes at least one sensor, such as a gyroscope, for determining rate of change of angular orientation. In some embodiments, only one of the anastomosis device components 110 includes a fine alignment module 225. For instance, in the example of FIG. 2, the fine alignment module 125 is included in the first anastomosis device component 110A. However, in other embodiments, the fine alignment module 125 is included in the second anastomosis device component 110B instead. In yet other embodiments, both the first anastomosis device component 110A and the second anastomosis device component 110B include a fine alignment module 225. In other embodiments, the two device components 110A and 110B are connected and can bring about a therapeutic effect on a stricture or similar etiology.

The fine alignment module 225 may include force sensors, electromagnetic sensors, magnetic sensors, SpO2 sensors, etc. For example, the force sensor measures a force being exerted by the coupling modules 230 of the first anastomosis device component 110A and the second anastomosis device component 110B. Based on the amount of force, a distance between the first anastomosis device component 110A and the second anastomosis device component 110B can be determined. In some embodiments, the fine alignment module 225 includes multiple force or magnetic field sensors, such as Hall effect sensors. Each sensor may be used to determine a distance between the first anastomosis device component 110A and the second anastomosis device component 110B at different location.

The wireless transmitter 245 sends data wirelessly to the wireless receiver 265 of the hub 250. The wireless transmitter 245 is configured to receive sensor data from the coarse alignment module 220 and the fine alignment module 225, encode the received data based on a predetermined wireless communication protocol, and wirelessly transmit the encoded signals. In some embodiments, the wireless transmitter 245 is configured to use a wireless communication protocol that is optimized for low power consumption. In some embodiments, the wireless transmitter 245 is configured for transmission through the tissues of the body. In some embodiments, the wireless transmitter 245 is configured to communicate with an intermediary wireless transmitter to overcome losses with passage of electromagnetic radiation, such as electromagnetic radiation at or around 2.4 GHz, through the body.

The coupling module 230A of the first anastomosis device component 110A is configured to interact with the coupling module 230B is of the second anastomosis device component 110B. The coupling module 230A of the first anastomosis device component 110A and the coupling module 230B of the second anastomosis device component 110B generate attractive forces that cause the first anastomosis device component 110A and the second anastomosis device component 110B to be attracted to each other. For example, each of the coupling module 230 may include one or more magnets that generate magnetic fields that cause the first anastomosis device component 110A to be attracted to the second anastomosis device component 110B.

The anastomosis module 235 creates an anastomosis by acting on the walls of the first lumen 120A and the second lumen 120B. In some embodiments, the anastomosis module 235 acts in place of sutures or staples in holding together the walls of the first lumen 120A and the second lumen 120B. In some embodiments, the anastomosis module 235 cauterizes the walls of the first lumen 120A and the second lumen 120B. In other embodiments, the anastomosis module 235 cuts the walls of the first lumen 120A and the second lumen 120B. In yet other embodiments, the anastomosis module 235 causes certain regions of tissue interposed between portions of the first anastomosis device component 110A and portions of the second anastomosis device component 110B to necrotize (e.g., by restricting blood flow through the application of pressure to the tissue). In some embodiments, the anastomosis module 235 is configured to be activated after the first anastomosis device component 110A is aligned to the second anastomosis device component 110B. Moreover, the anastomosis module 235 may be configured to be activated after the first anastomosis device component 110A and the second anastomosis device component 110B are locked in place by their respective coupling modules 225. In some embodiments, the anastomosis module 235 includes a tissue modification element (such as blade or a picosecond laser) for modifying the tissue of the walls of the first lumen 120A and the second lumen 120B.

Anastomosis creation can occur over a period of hours or days, as the tissue interposed between the mated first anastomosis device component and second anastomosis device component undergoes physiological changes in response to the force applied by the tissue-contacting surfaces of the first and second anastomosis device components. The physiological process known as neoepithelization can occur where two layers of tissue are held in contact with one another. Progressive peripheral neoepithelization and central necrosis at the location where the first lumen 120A and the second lumen 120B are in contact can, over a period of time can result in formation of a healthy lumen between the first lumen 120A and the second lumen 120B.

In other embodiments, the functions of the anastomosis module 235 are performed by other components of the first anastomosis device component 110A and the second anastomosis device component 110B. For example, functions of the anastomosis device 235 may be performed by the coupling module 230A of the first anastomosis device component 110A and the coupling module 230B of the second anastomosis device component 110B. When the coupling module 230A of the first anastomosis device component 110A interacts with the coupling module 230B of the second anastomosis device component 110B, pressure is applied to the tissue trapped between the coupling module 230A of the first anastomosis device component 110A and the coupling module 230B of the second anastomosis device component 110B. The pressure applied to the tissue causes the tissue modification forming an anastomosis. For example, the pressure applied to the tissue may cause the tissue to necrotize. Additionally, the applied pressure may cause the walls of the first lumen 120A and the second lumen 120B to fuse around the necrotized tissue.

The power module 240 receives power wirelessly from the wireless power transmitter 260 and delivers power to the various components of the anastomosis device component 110. For example, the power module 240 includes circuitry for regulating the power received from the wireless power transmitter 260 and generating a substantially constant voltage for powering the coarse alignment module 220, the fine alignment module 225, and the anastomosis module 235.

In some embodiments, the power module 240 includes a battery. The battery is configured to provide power to the various components of the anastomosis device components 110 (e.g., in addition to or instead of the energy received from the wireless power transmitter 260). In some embodiments, the components of the anastomosis device components 110 are turned off or places in a low power mode (e.g., sleep mode) to conserve power. For example, during specific stages of the anastomosis process, certain components or modules of each of the anastomosis device components 110 are turned off (e.g., by turning off components that are not in use during each of the stages of the anastomosis process). In some embodiments, the battery is charged prior to the start of the anastomosis process (e.g., prior to inserting the anastomosis device components 110 inside the body of a patient). Moreover, in some embodiments, the battery is charged wirelessly using the power received from the wireless power transmitter 260.

The hub 250 includes a wireless power transmitter 260, a wireless receiver 265, an effector 270, a catheter 275, a controller 280, and an input-output (0/I) module. In some embodiments, the hub 250 allows for an operator to interact with the first and second anastomosis device components 110. Alternatively, the hub 250 operates in an autonomous mode and performs an anastomosis using the first and second anastomosis device components 110 without the intervention of a human operator. Moreover, in some embodiments, one or more components of the hub 250 (such as portions of the controller 280) are embedded in the first anastomosis device component 110A or the second anastomosis device component 110B.

The wireless power transmitter 260 provides power to the power modules 240 of the first and second anastomosis device components 110. In some embodiments the wireless power transmitter 260 includes multiple antennas allow the first and second anastomosis device components 110 to receive power at different location within the body of a patient. In some embodiments, the wireless power transmitter 260 receives information about the expected power consumption of the first and second anastomosis device components 110 and transmits a wireless signal having an amount of power determined based at least on the expected power consumption of the first and second anastomosis device components 110.

The wireless receiver 265 receives wireless signals from the wireless transmitter 245 of the first and second anastomosis device components 110. The wireless receiver 265 communicates with the wireless transmitters 245 of the first and second anastomosis device components 110 using a predetermined wireless communication protocol. In some embodiments, the wireless receiver 265 decodes the signals received form the wireless transmitters 245 of the first and second anastomosis device components 110 and provides the decoded signals to the controller 280.

The effector 270 allows for the hub 250 to physically interact with the first and second anastomosis device components 110. The effector 270 may be part of a surgical robotic system. In some embodiments, the effector 270 may be able to push, pull, or press the first or second anastomosis device components 110 to control the position of the first and second anastomosis device components 110.

The catheter 275 attaches to the first anastomosis device component 110A or the second anastomosis device component 110B to insert the first anastomosis device component 110A or the second anastomosis device component 110B into the body of the patient. In some embodiments, the anastomosis system 210 includes at least two catheters 275 (i.e., a first catheter for inserting the first anastomosis device component 110A and a second catheter for inserting the second anastomosis device component 110B). In some embodiments, positioning of an anastomosis device component within the body makes use of peristalsis occurring within the patient's gastrointestinal tract.

The controller 280 receives sensor information corresponding to data captured by the course alignment module 220 and the fine alignment module 225 of the first anastomosis device component 110A and the second anastomosis device component 110B. In addition, the controller 280 receives user inputs provided by the user through the I/O module 285. Based on the received sensor information and the received user input, the controller 280 generates a set of instructions for controlling the various components of the anastomosis system 200. For example, the controller 280 generates a set of instructions for controlling the effectors for physically interacting with the first anastomosis device component 110A or the second anastomosis device component 110B. In another example, the controller 280 generates a set of instructions for displaying information to an operator through the I/O module 285 (e.g., through a monitor of the hub 250). In some embodiments, an intermediary module relays signals between anastomosis device components and the hub.

Coupling Module

Each anastomosis device component 110 has a coupling module 230 that is configured to interact with a coupling module 230 of another anastomosis device component 110. In some embodiments, the coupling modules 230 are configured to interact at a distance. That is, a coupling module 230 of a first anastomosis device component 110 is configured to exert a force at a distance (i.e., without being in contact with) the coupling module 230 of a second anastomosis device component 110. In some embodiments, the coupling modules 230 include magnets or electromagnets to enable the coupling modules 230 to interact at a distance.

Moreover, the anastomosis device components 110 have one or more surfaces (e.g., tissue-contacting surfaces or faces) that are configured to match a surface of a second anastomosis device component 110. The first and second anastomosis device components 110 may be configured to be similar in size to each other and may be designed each with a flat surface, where the two flat surfaces mate (with the tissue sitting in between the surfaces). As another example, a first anastomosis device component 110A includes a bottom surface having a shape corresponding to a top surface of a second anastomosis device component 110B. For instance, the bottom surface of first anastomosis device component 110A can have a convex surface configured to interact with the top surface of the second anastomosis device component 110B having a concave surface. The radii of the convex and concave surfaces can differ. In some embodiments, a tissue-contacting surface of an anastomosis device components 110 has an approximately circular shape. In some embodiments, the tissue-contacting surface of the anastomosis device components 110 have a diameter between 1 mm and 50 mm.

In some embodiments, the coupling module 230 and the outer shape of the anastomosis device components are designed to configure a first anastomosis device component 110A to align to a second anastomosis device component 110B. FIG. 3A illustrates a coupling module 230A of a first anastomosis device component 110A interacting with a second coupling module 230B of a second anastomosis device component 110B, according to one or more embodiments. FIG. 3B illustrates a pair of anastomosis device components 110 having an axial misalignment, according to one or more embodiments. FIG. 3C illustrates a pair of anastomosis device components 110 having a lateral misalignment, according to one or more embodiments. FIG. 3D illustrates a first anastomosis device component 110A aligned to a second anastomosis device component 110B, according to one or more embodiments.

The coupling module 230A of the first anastomosis device component 110A includes one or more magnets (or electromagnets) 310A configured to attract one or more magnets 310B of the coupling module of the second anastomosis device component 110B. As such, the coupling module 230B of the second anastomosis device component 110B induces an attractive force 315 on the coupling module 230A of the first anastomosis device component 110A to cause the first anastomosis device component 110A to move towards the second anastomosis device component 110B. Similarly, the coupling module 230A of the first anastomosis device component 110A induces an attractive force 315 on the coupling module 230B of the second anastomosis device component 110B to cause the second anastomosis device component 110B to move towards the first anastomosis device component 110A. In some embodiments, the one or more magnets of the first anastomosis device component 110A and/or the one or more magnets of the second anastomosis device components are selected such that when the tissue-contacting faces of the first anastomosis device component and the second anastomosis device component are separated by 4 mm, the force between the first anastomosis device component and the second anastomosis device component is between 0.2 Newtons and 20 Newtons. In some embodiments, one of the anastomosis modules comprises a permanent magnet and another anastomosis module comprises a magnetic material. In some embodiments, the magnetic material is a ferrofluid.

In some embodiments, the magnets are permanent magnets that do not consume energy. This might be beneficial to reduce the overall power consumption of the anastomosis device components 110 and to reduce the overall size of the anastomosis device components 110. The devices can also comprise multiple magnetic elements that can be reconfigured to increase or decrease the magnetic force. For example, half-toroid magnets with opposing polarities can be nested and rotated relative to one another to increase or decrease the magnetic. Alternatively, the magnets are electromagnets that can be turned on or off. Moreover, the magnetic field of each magnet may be controlled to increase or decrease the amount of force one coupling module 230A induces on another coupling module 230B.

FIGS. 3E and 3F illustrate magnetic elements including a first magnetic anchor and a second magnetic anchor that can be controlled to increase or decrease the magnetic force between the first and second magnetic anchors, according to one or more embodiments. In the example of FIG. 3E, the first magnetic anchor 350 (e.g., the magnet included in the first anastomosis device component 110A) has a first polarity and is configured to interact with a second magnetic anchor 360 (e.g., the magnet included in the second anastomosis device component 110B). The second magnetic anchor may include a first portion 362 and a second portion 364. The first portion 362 and the second portion 364 may be configured to have a second polarity (opposite of the first polarity) configured to attract the first magnetic anchor having the first polarity. Moreover, the second portion may be controlled to increase or decrease the attractive force between the first magnetic anchor and the second magnetic anchor. For example, the second portion 364 may be removed to decrease the attractive force between the first magnetic anchor and the second magnetic anchor. Alternatively, a height of the second portion may be controlled to modulate the attractive force between the first magnetic anchor and the second magnetic anchor.

In the example of FIG. 3F, the first magnetic anchor 370 (e.g., the magnet included in the first anastomosis device component 110A) has a first portion 372 having a first polarity, and a second portion 374 having a second polarity. Moreover, the second magnetic anchor 380 has a first portion having the second polarity and configured to attract the first portion of the first magnetic anchor, and a second portion having the first polarity and configured to attract the second portion of the first magnetic anchor. Additionally, the second magnetic anchor includes a third portion 392 having the second polarity and a fourth portion 394 having the first polarity. The third and fourth portions of the second magnetic anchor are configured to rotate to modulate an amount of force between the first magnetic anchor 370 and the second magnetic anchor 380. For instance, the third portion 392 of the second magnetic anchor is configured to attract the first portion of the first magnetic anchor and repel the second portion of the first magnetic anchor. The fourth portion 394 of the second magnetic anchor, is configured to attract the second portion of the first magnetic anchor and repel the first portion of the first magnetic anchor. As such, the force between the first magnetic anchor and the second magnetic anchor can be modulated by rotating the third and fourth portions of the second magnetic anchor. As shown in FIG. 3F, the second magnetic anchor is at full strength when the third portion of the second magnetic anchor is aligned with the first portion of the first magnetic anchor and the fourth portion of the second magnetic anchor is aligned with the second portion of the first magnetic anchor. Moreover, the second magnetic anchor is at its least strength when the third portion of the second magnetic anchor is aligned with the second portion of the first magnetic anchor and the fourth portion of the second magnetic anchor is aligned with the first portion of the first magnetic anchor.

Moreover, the first anastomosis device component 110A includes a first outer surface 320A (e.g., a bottom surface) and a second outer surface 325A (e.g., a top surface) opposite to the first surface and connected to the first surface through a side surface 330A. The second anastomosis device component 110B includes a first outer surface 320B (e.g., a top surface) and a second outer surface 325B (e.g., a bottom surface) opposite to the first surface and connected to the first surface through a side surface 330B. The first outer surface 320A of the first anastomosis device component 110A is configured to couple with the first outer surface 320B of the second anastomosis device component 110B.

For example, the surface 320A of the first anastomosis device component 110A has a shape that conforms to the shape of the outer surface 320B of the second anastomosis device component 110B. Thus, as the force induced by the coupling modules 310A and 310B cause the anastomosis device components 110A and 110B to get close to each other, the anastomosis devices move in a manner that causes the outer surface 320A of the first anastomosis device component 110A to align with the corresponding outer surface 320B of the second anastomosis device component 110B.

For example, FIG. 3B illustrates an example of a pair of anastomosis devices 110A and 110B having an axial misalignment. In this example, the coupling module 230B of the second anastomosis device component 110B induces a force 315 on the coupling module 230A of the first anastomosis device component 110A to cause the axis of the first anastomosis device component 110A to rotate counterclockwise relative to the xz axis (where the z axis is the vertical axis in this depiction and the x axis is the horizontal axis in this depiction). Similarly, the coupling module 230A of the first anastomosis device component 110A induces a force 315 on the coupling module 230B of the second anastomosis device component 110B to cause the second anastomosis device component 110B to rotate in the clockwise direction relative to the xz axis.

In another example, FIG. 3C illustrates an example of a pair of anastomosis device components 110A and 110B having a lateral misalignment. In this example, the coupling module 230B of the second anastomosis device component 110B induces a force 315 on the coupling module 230A of the first anastomosis device component 110A to cause the first anastomosis device component 110A to move laterally to the right with respect to the second anastomosis device component 110B. Similarly, the coupling module 230A of the first anastomosis device component 110A induces a force 315 on the coupling module 230B of the second anastomosis device component 110B to cause the second anastomosis device component 110B to move laterally to the left with respect to the first anastomosis device component 110A. In some embodiments, the shape of the outer surfaces of the first anastomosis device component 110A and the second anastomosis device component 110B further aids the lateral movement of the anastomosis device components. For example, the outer surfaces 320 of the anastomosis device components 110 include slanted portions that aid the lateral movement of the anastomosis device components 110.

In addition, once the first anastomosis device component 110A is engaged with the second anastomosis device component 110B, the coupling module 230 of the first and second anastomosis devices 110 induce an attractive force between each other to keep the first anastomosis device component 110A engaged with the second anastomosis device component 110B. In some embodiments, if the coupling modules 230 include electromagnets, a current provided to the electromagnets may be reduced once the first anastomosis device component 110A is engaged with the second anastomosis device component 110B to lower the power consumption of the anastomosis device components.

In some embodiments, the first anastomosis device can include a structure (such as a balloon) that can be filled with a gas or liquid (e.g., a saline solution). Similarly, the second anastomosis device component includes a structure that can be filled with a gas or liquid. The fillable structure can be affixed to the magnetic elements of the first anastomosis device component 110A, the second anastomosis device component 110B, or both. The fillable structure can enclose the magnetic elements of the first anastomosis device component 110A, of the second anastomosis device component 110B, or both. The fillable structure in the first anastomosis device and the structure in the second anastomosis device may be able to enlarge and become rigid upon forcing a gas or liquid into the structures. The fillable structure can, when unfilled, have a compact configuration. For example, the fillable structure's material may be configured to lay flat against a magnetic element. In some embodiments, the structures are made of nylon. In some embodiments, the structures are designed to be filled with a ferrofluid.

In some embodiments, the first anastomosis device component includes a mesh or woven structure that can be transitioned between a deployment configuration and a therapeutic configuration. Similarly, the second anastomosis device component includes a mesh or woven structure that can be transitioned between a deployment configuration and a therapeutic configuration. In some embodiments, in the therapeutic configuration, the first anastomosis device component has a flange shape. Moreover, in the therapeutic configuration, the second anastomosis device component has a flange shape and an adjoining cylindrical region.

Coarse and Fine Alignment Module

To align the first anastomosis device component 110A and the second anastomosis device component 110B prior to operating the anastomosis device components 110 to create an anastomosis, a set of alignment modules are used. In some embodiments, a coarse alignment module 220 and a fine alignment module 225 are used.

In some embodiments, the coarse alignment module 220 and the fine alignment module 225 are used sequentially. The coarse alignment module 220 is used to control or monitor the position of the anastomosis device components 110 until the first anastomosis device component 110A and the second anastomosis device component 110B meet inside the body of a patient.

Figure 4:
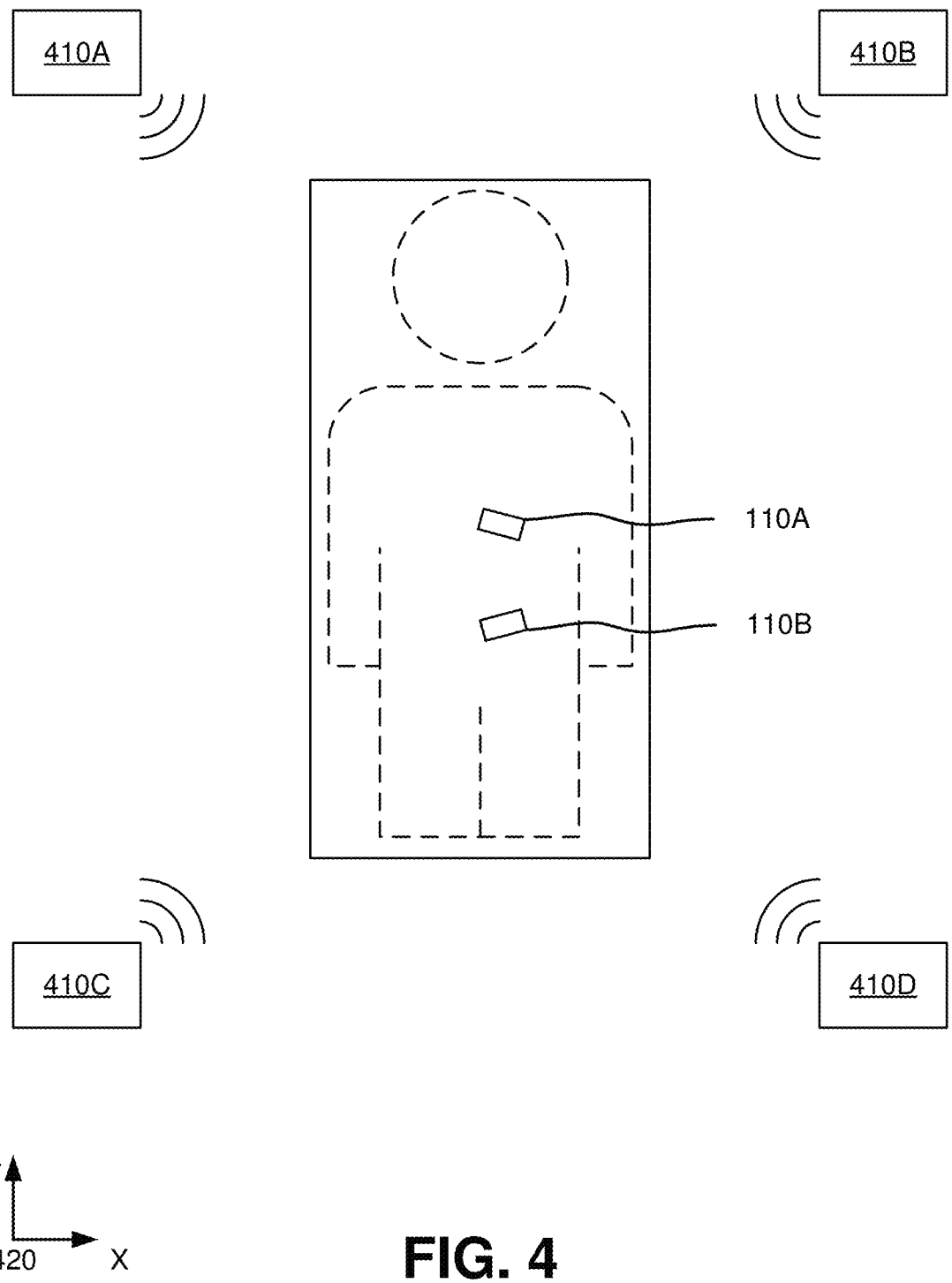
FIG. 4 illustrates a system for determining the position of the anastomosis device components, according to one or more embodiments.

In some embodiments, the coarse alignment module 220 tracks the position of each anastomosis device component 110 within the body of the patient using a global frame of reference. FIG. 4 illustrates a system for determining the position of the anastomosis device components 110, according to one or more embodiments. For example, the global frame of reference 420 is set by a set of locators 410 located outside of the body of the patient. Each of the coarse alignment modules 220 receives the signals sent by the locators 410 located outside of the body of the patient and determines the location of the anastomosis device component based on the received signals. In an alternative embodiment, each of the coarse alignment modules 220 transmits a signal that is received by locators and sent to the controller 280 of the hub 250. The controller 280 is then able to determine the position of each of the anastomosis modules based on properties of the received signals (e.g., signal strength, signal delay, and the like). In some embodiments, the controller 280 determines the position of each of the anastomosis device components 110 based on a difference between the signals received by each of the locators 410 for a specific anastomosis device component 110.

In some embodiments, the coarse alignment module 220 includes sensors for aiding the determination of the position of each of the anastomosis device components 110. For example, the coarse alignment module 220 includes a set of accelerometers and gyroscopes that may be used to determine the position of the anastomosis device components 110 by calculating an amount of translation and rotation of the anastomosis device component 110 from an initial position. In some embodiments, the anastomosis device components 110 transmits the sensor data using the wireless transmitter 245. The sensor data is then wirelessly received by the hub 250 via the wireless receiver 265 and provided to the controller 280 to allow the controller 280 to determine the position of the anastomosis module 110.

In some embodiments, the coarse alignment module 220 further includes one or more cameras. The cameras may be used to capture images of the surroundings of the anastomosis device components 110 to allow the anastomosis devices to identify obstacles in the vicinity of the anastomosis device component 110 that may be impeding the movement of the anastomosis device components 110.

In some embodiments, the hub 250 displays the position of the anastomosis device components 110 in a display device of the I/O module 285. For example, the hub 250 may display the coordinates of each of the anastomosis device components, a distance between the anastomosis device components, or may plot the position of each of the anastomosis device components 110 in the global frame of reference 420. For example, the hub may overlay the plot of the position of the anastomosis device components to an image or video feed that is aligned to the global frame of reference 420. The image can be preoperative imaging, such as an x-ray or CT scan. As another example, the hub may display the position and orientation of the anastomosis device components in a three-dimensional virtual reality environment.

Alternatively, the controller 280 hub controls the catheter 275 based on the determined position of the anastomosis device component 110. The catheter 275 is configured to move the anastomosis device component 110 to a predetermined location within the body of the patient. In some embodiments, the anastomosis device component 110 is attached to an end of the catheter 275.

Although the hub may be able to determine that the first anastomosis device component 110A has engaged with the second anastomosis device component 110B, because of the resolution of the coarse adjustment module 220, the hub 250 may not be able to determine misalignments between the first anastomosis device component 110A and the second anastomosis device component 110B beyond a certain resolution. In some instances, the misalignment between the first anastomosis device component 110A and the second anastomosis device component 110B may be caused by matter being trapped in between the first anastomosis device component 110A and the second anastomosis device component 110B.

Figure 5A:
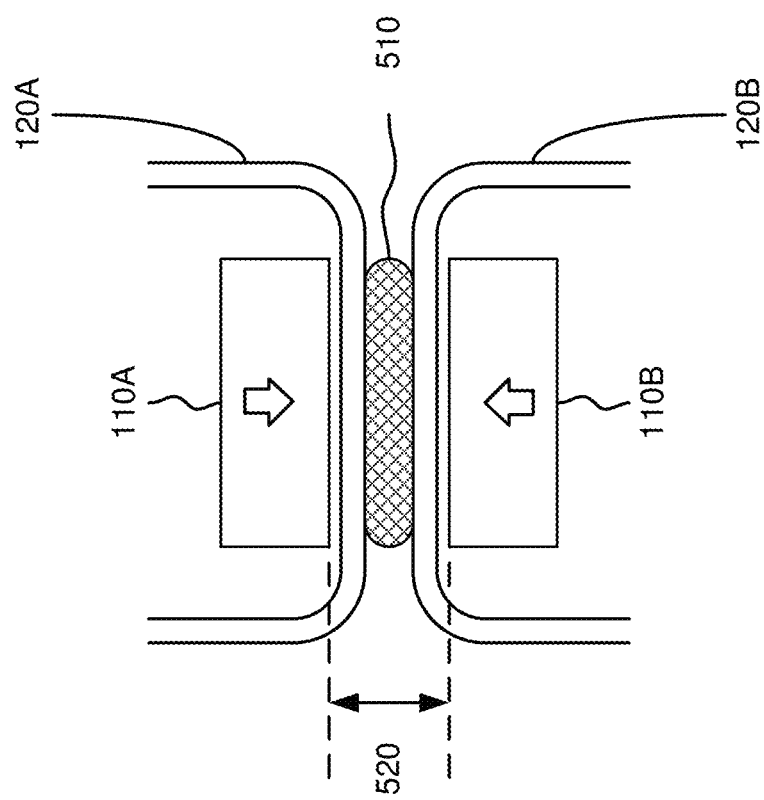

FIGS. 5A and 5B illustrate examples of situations when the first anastomosis device component 110A and the second anastomosis device component 110B are misaligned. In the example of FIG. 5A, matter 510 is trapped between the first lumen 120A and the second lumen 120B. In the example of FIG. 5B, the walls of the lumens 120 may have irregular thickness. For example, when creating an anastomosis in the small intestine of the patient, portions of the mesentery may get trapped in between the first anastomosis device component 110A and the second anastomosis device component 110B. In another example, the walls of the lumens 120 may contain fibrotic tissue that may be trapped in between first anastomosis device component 110A and the second anastomosis device component 110B.

The trapped matter 510 may prevent the first anastomosis device component 110A from fully engaging with the second anastomosis device component 110B, possibly causing a reduction in the quality of the anastomosis created by the first anastomosis device component 110A and the second anastomosis device component 110B. As shown in FIG. 5A, the trapped matter 510 may increase the gap or distance 520 between the first anastomosis device component 110A and the second anastomosis device component 110B compared to an expected gap or distance when only the walls of the lumens are in between the first anastomosis device component 110A and the second anastomosis device component 110B. Moreover, as shown in FIG. 5B, the trapped matter 510 may cause the first anastomosis device component 110A and the second anastomosis device component 110B to engage at an angle 525.

In some instances the increase in the distance 520 between the first anastomosis device component 110A and the second anastomosis device component 110B, or the angle 525 between the first anastomosis device component 110A and the second anastomosis device component 110B may be smaller than resolution of the coarse alignment module 220. As such, the hub may not be able to detect the increase in the distance 520 between the first anastomosis device component 110A and the second anastomosis device component 110B or the angle 525 between the first anastomosis device component 110A and the second anastomosis device component 110B based on data receive from the coarse alignment module 220.

Thus, once the anastomosis device components 110 have been placed in a predetermined position within the body of the patient, the fine adjustment module 225 is used to identify misalignments between the first anastomosis device component 110A and the second anastomosis device component 110B. In some embodiments, the fine adjustment module 225 is activated or turned on once the hub determines that the first and second anastomosis devices 110 have started engaging with each other. For example, fine adjustment module 225 is turned on when the hub determines that the first anastomosis device component 110A is within a threshold distance from the second anastomosis device component 110B.

In some embodiments, the fine adjustment module 225 has one or more sensors for determining a distance between the first anastomosis device component 110A and the second anastomosis device component 110B. The sensors may include multiple sensors located at different portions within the anastomosis device component 110. Each sensor may then be used for determining multiple distance between the first anastomosis device component 110A and the second anastomosis device component 110B. The multiple distances may then be used for determining an angle between the first anastomosis device component 110A and the second anastomosis device component 110B.

In some embodiments, the sensors are force sensors. The force sensors are configured to sense a force exerted to the anastomosis device component 110 as the coupling module 225 of the anastomosis device component 110 is attracted to the coupling module 225 of another anastomosis device component 110. As the distance between the pair of anastomosis devices 110 decrease, the force induced by the coupling modules 230 increases. Thus, the controller 280 of the hub 250 is able to estimate the distance between a pair of anastomosis device components 110 based on the magnitude of the force sensed by the force sensors.

In some embodiments, the fine alignment module 225 is provided in only one anastomosis device component 110 of a pair of anastomosis device components. In other embodiments, the fine adjustment module 225 is provided in both anastomosis device components 110 of the pair of anastomosis device components. In some embodiments, to reduce power consumption of the anastomosis device components, the coarse adjustment module 230 and the fine adjustment module 225 are turned on or off at different steps of a procedure. For example, before the anastomosis device components 110 are not engaged with each other, the fine alignment module 225 is turned off. Subsequently, once the anastomosis device components 110 engage with each other, the coarse alignment module 230 is turned off and the fine adjustment module is turned on. In some embodiments, the coarse alignment module 230A module of the first anastomosis device component 110A is turned off, the fine alignment module 225 of the first anastomosis device component 110A, and the coarse alignment module 230B of the second anastomosis device component 110B is kept on. Since the first anastomosis device component 110A is engaged with the second anastomosis device component 110B, the position of the first anastomosis device component 110A may be determined based on the position of the second anastomosis device component 110B.

FIG. 6A illustrate a diagram of a pair of anastomosis device components 110 having a first distance, according to one or more embodiments. FIG. 6B illustrate a diagram of a pair of anastomosis device components 110 having a second distance, according to one or more embodiments. In particular, the distance D2 between the pair of anastomosis device components 110 in the example of FIG. 6B is smaller than the distance D1 between the pair of anastomosis device components 110 in the example of FIG. 6A. Thus, the force F1 induced by the coupling module 230B of the second anastomosis device component 110B on the coupling module 230A of the first anastomosis device component 110A in the example of FIG. 6A is smaller than the force F2 induced by the coupling module 230B of the second anastomosis device component 110B on the coupling module 230A of the first anastomosis device component 110A in the example of FIG. 6B.

In some embodiments, the hub 250 displays the force F sensed by the sensors of the fine alignment module 225. In other embodiments, the hub 250 displays the estimated distance D calculated based on the force F sensed by the sensors of the fine alignment module 225. For example, the hub 250 displays the force F or the distance D through a display device of the I/O module 285.

FIG. 7A illustrate a diagram of a pair of anastomosis device components 110 having an angle φ1, according to one or more embodiments. FIG. 7B illustrate a diagram of a pair of anastomosis device components 110 parallel to each other, according to one or more embodiments. In the example of FIG. 7A, since the first anastomosis device component 110A is at an angle with respect to the second anastomosis device component 110B, the first sensor 610A and the second sensor 610B sense forces having different magnitudes. In contrast, in the example of FIG. 7B, since the first anastomosis device component 110A is parallel to the second anastomosis device component 110B, the first sensor 610A and the second sensor 610B sense forces having substantially the same magnitudes. In some embodiments, the controller 280 of the hub 250 calculates an estimated angle between the first anastomosis device component 110A and the second anastomosis device component 110B based on the force sensed by the first sensor 610A, the force sensed by the second sensor 610B, and the distance between the first sensor 610A and the second sensor 610B.

Effector

The fine alignment module 220 may be used to control the effector 270. In some embodiments, the hub 250 presents information about the alignment of the pair of anastomosis device components 110 and the operator of the hub 250 provides instruction on how to control the effector through the I/O module 285. For example, the operator may provide instructions on how to move the effector to improve the alignment of the pair of anastomosis device components 110.

In other embodiments, the controller 280 of the hub 250 automatically controls the effectors 270 based on the alignment information and information about the position of each of the anastomosis device components 110. For example, the controller 280 determines a trajectory for moving the effector 270 to change the position or alignment of the pair of anastomosis device components 110. In some embodiments, the effector 270 has one or more cameras (such as a tip mounted camera). The images captured by the cameras of the effector are provided to the controller 280 to allow the controller to identify in the vicinity of the effector 270. For example, the controller 280 uses one or more image recognition algorithms to detect the anastomosis device components 110 to determine the position of the anastomosis device components 110 relative to the effector 270. Moreover, the controller 280 uses one or more image recognition algorithms to detect obstacles that may impede the movement of the effector 270 based on the determined trajectory for the effector.

Figure 8A:
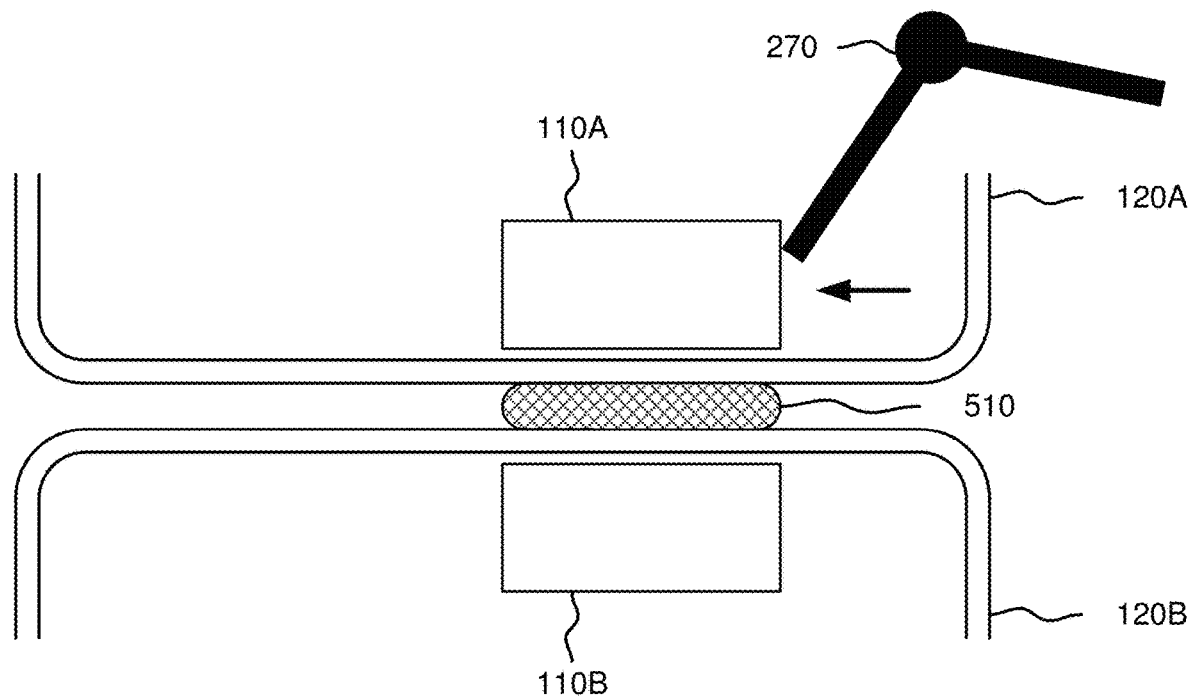
FIGS. 8A and 8B illustrate a first example of an effector translating a pair of anastomosis device components, according to one or more embodiments.
Figure 8B:
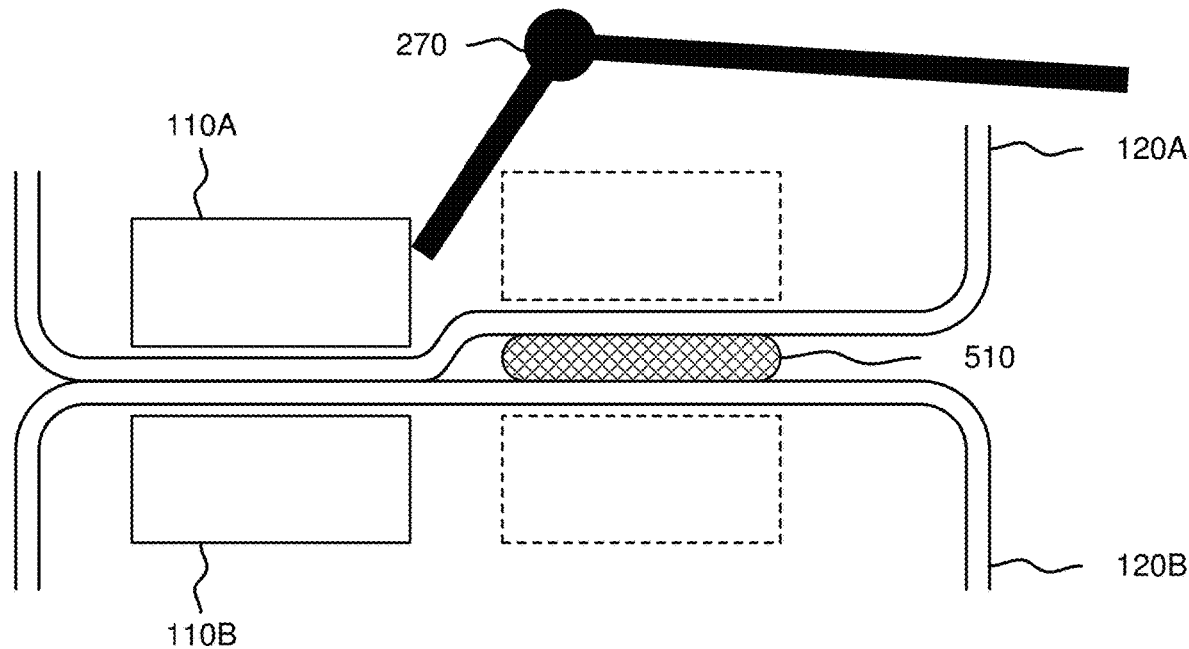

FIGS. 8A and 8B illustrate a first example of an effector translating a pair of anastomosis device components 110, according to one or more embodiments. In the example of FIGS. 8A and 8B, an area of mesentery is trapped in between the pair of anastomosis device components 110, increasing the distance between the anastomosis device components. Based on the information captured by the coarse alignment module 230, the fine alignment module 225, and other sensor information such as images captured by a tip mounted camera of the effector 270, the controller 280 generates a trajectory for the effector to translate the pair of anastomosis device components 110 to the left such that the area of mesentery tissue is no longer between the two devices 110, and instead there is only lumen walls between the devices. It is beneficial to move the devices away from a position where the section of mesentery is trapped between them for a couple of reasons. First, where there is mesentery trapped between the devices, this tends to slow the anastomosis formation because the mesentery must be necrosed in addition to the lumen walls. Second, the anatomy after healing may be unfavorable from the standpoint of susceptibility to an internal hernia. Thus, in FIG. 8B, the devices have been repositioned to a location where they are mated without intervening mesentery. In some embodiments, the controller modifies the trajectory based on new sensor data received as the anastomosis device components 110 are moved.

Figure 9A:
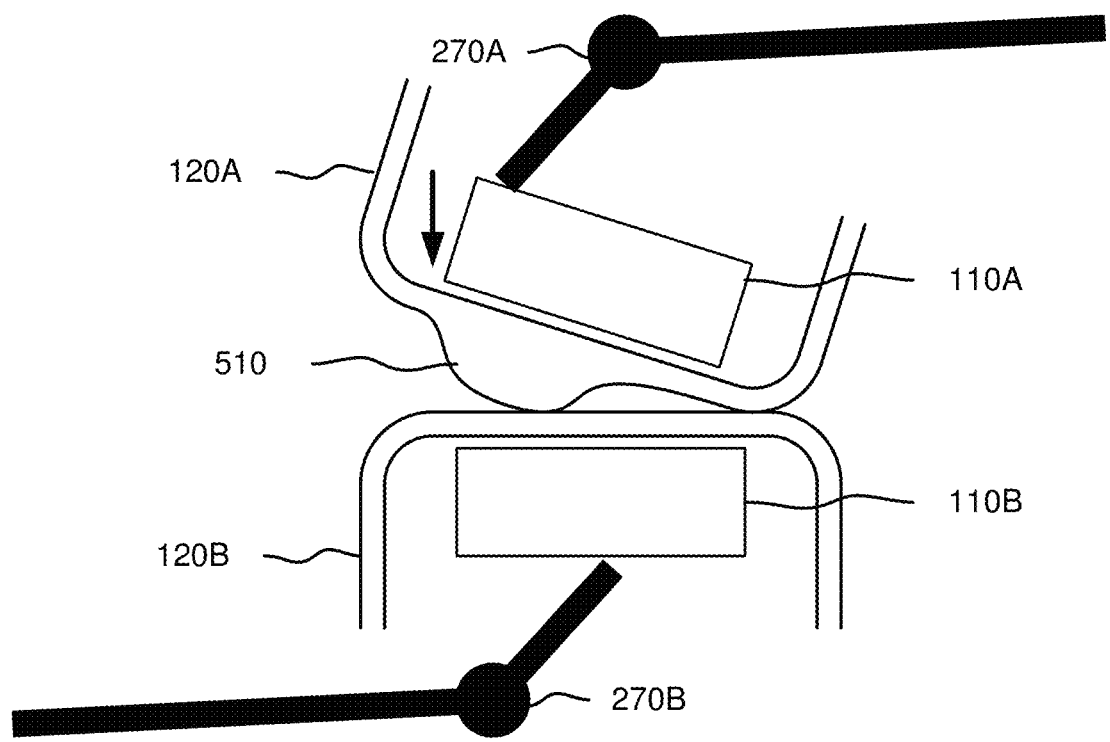
FIGS. 9A and 9B illustrate a first example of an effector rotating a pair of anastomosis device components, according to one or more embodiments.
Figure 9B:
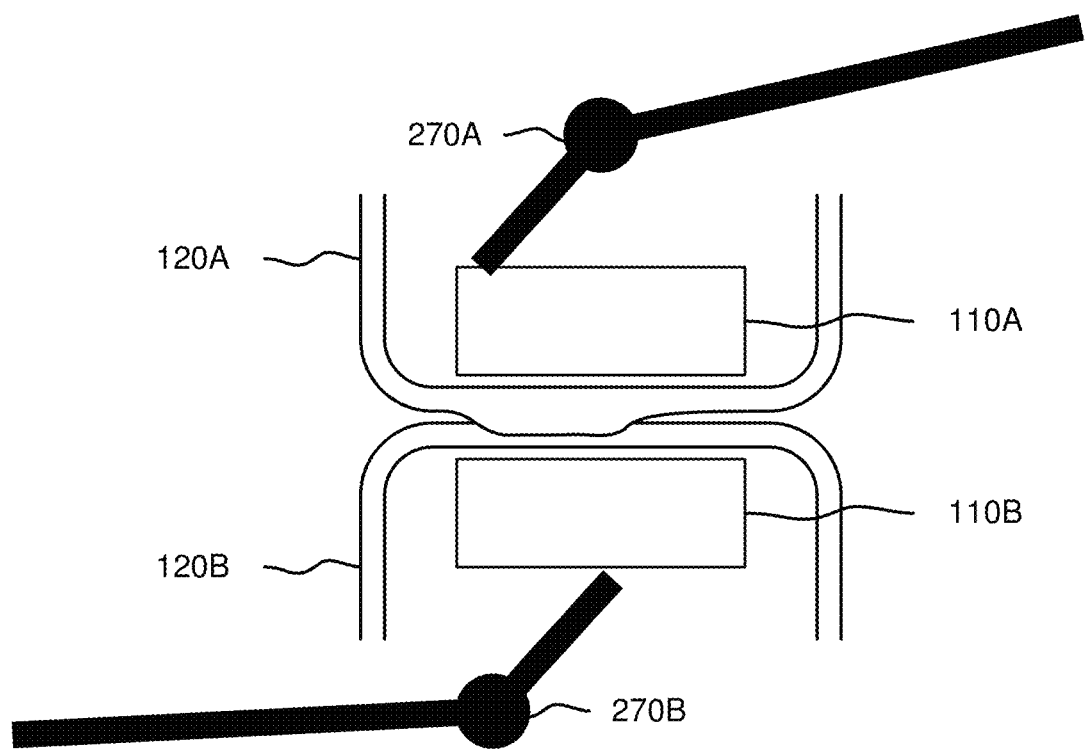

FIGS. 9A and 9B illustrate a first example of an effector rotating a pair of anastomosis device components 110, according to one or more embodiments. In the example of FIGS. 9A and 9B, fibrotic tissue 910 is trapped in between the pair of anastomosis device components 110, increasing the distance between the anastomosis device components and causing the anastomosis device components to engage at an angle. Based on the information captured by the coarse alignment module 230, the fine alignment module 225, and other sensor information such as images captured by a tip mounted camera of the effector 270, the controller 280 generates a trajectory for the effector to compress the fibrotic tissue 910. In some embodiments, multiple effectors are used for compressing the fibrotic tissue 910. In this embodiment, the controller 280 determines a trajectory for each of the effectors. For example, the controller 280 determines a trajectory for a first effector to manipulate a first end of the first anastomosis device component 110A, a trajectory for a second effector to manipulate a second end of the first anastomosis device component 110A, a trajectory for a third effector to manipulate a first end of the second anastomosis device component 110B, and a trajectory for a fourth effector to manipulate a second end of the second anastomosis device component 110B. In some embodiments, artificial intelligence or machine learning is used to guide, either directly or indirectly, the manipulation of anastomosis device components.

Wireless Power

Each anastomosis device component 110 includes a power module 240 for providing power to the various components of the anastomosis device component 110. In some embodiments, the power module 240 includes a battery for storing energy to be used by the anastomosis device components 110. Moreover, the power module 240 includes a wireless power receiver for receiving power wirelessly from the wireless power transmitter 260 of the hub 250.

Figure 10A:
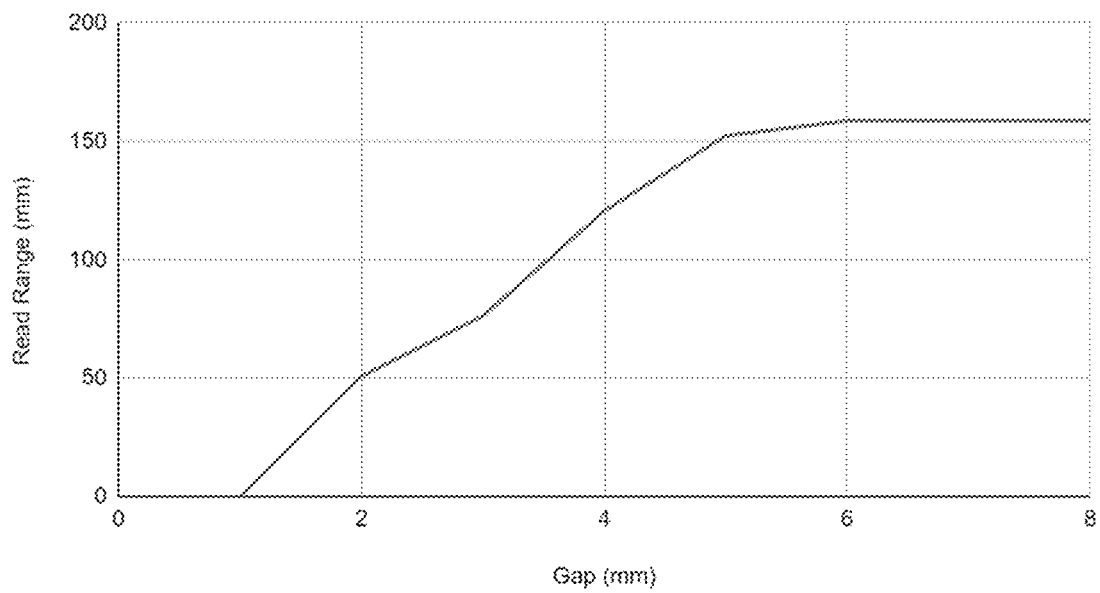
FIG. 10A illustrates a graph showing the range at which wireless power or data transfer to and from a component of the anastomosis device component may occur, according to one or more embodiments.

FIG. 10A illustrates a graph 1010 showing the range at which the various component of the anastomosis device component 110 (modeled as a 10 kΩ load) may be powered, according to one or more embodiments. In the example of FIG. 10A, the anastomosis device component is powered using an 8-watt RFID base station antenna. The graph 1010 shows the range as a function of a gap between a disk-shaped magnetic element and a 15 mm×15 mm device-integrated RFID antenna.

Figure 10B:
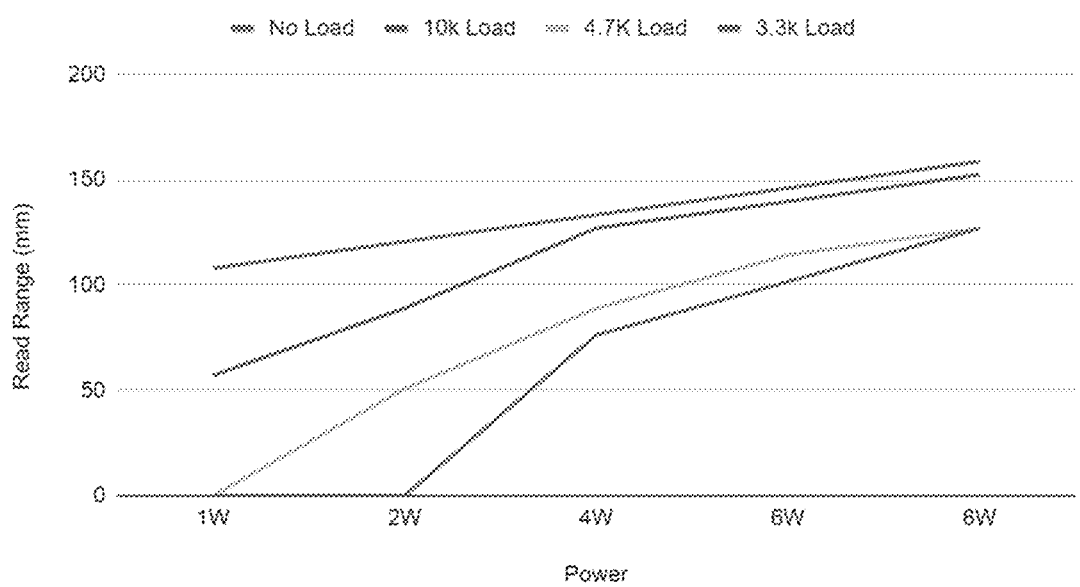
FIG. 10B illustrates a graph of ranges at which wireless power or data transfer to and from the various components of the anastomosis device component may occur, according to one or more embodiments.

FIG. 10B illustrates a graph 1020 of the range at which the various components of the anastomosis device component 110 (modeled as loads having different resistance values), according to one or more embodiments. The graph 1020 illustrates the range as a function of power provided to the wireless power transmitter 260 of the hub. As shown in FIG. 10B, as the load resistance and/or the power decreases, the range for operating the anastomosis device component also decreases.

Anastomosis System

Figure 11A:
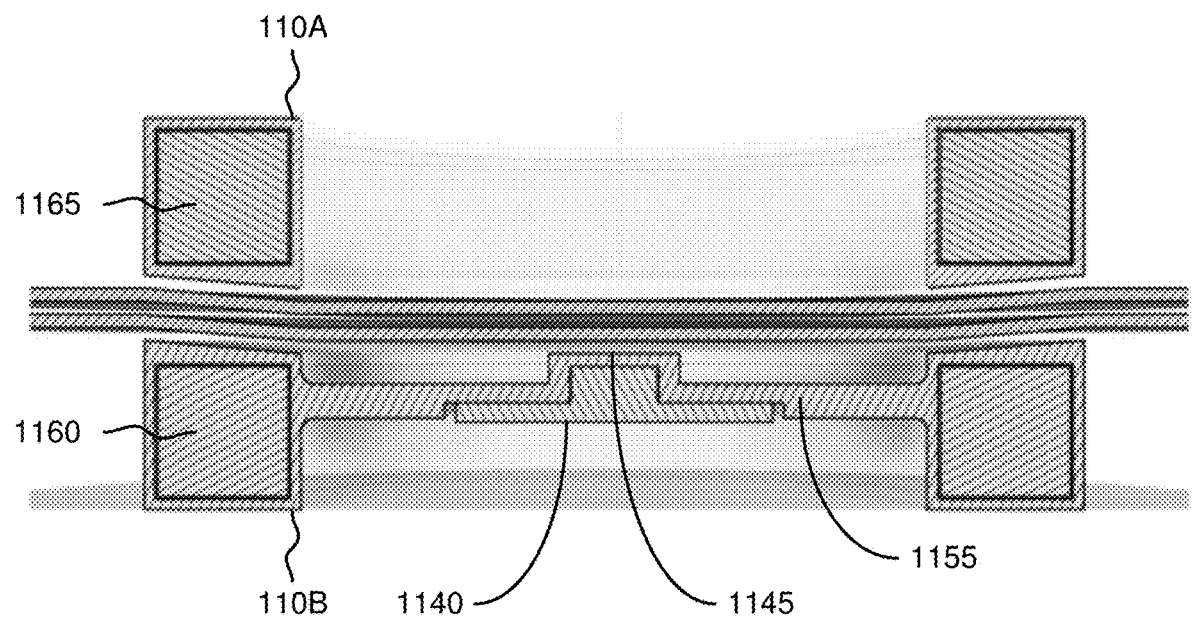
FIG. 11A is a cross-sectional view of pair of anastomosis device components, according to one or more embodiments.
Figure 11B:
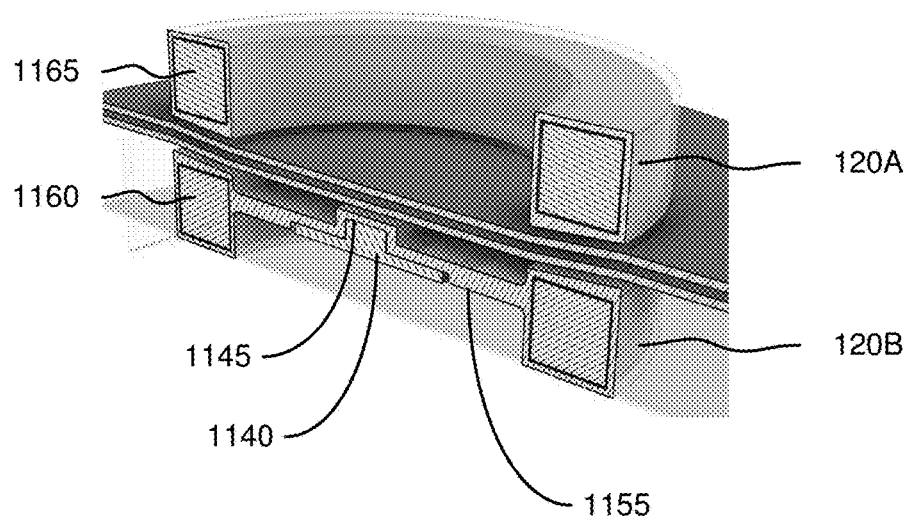
FIG. 11B is a plan view of the pair of anastomosis device components showing the cross section of the anastomosis device components, according to one or more embodiments.

FIG. 11A is a cross-sectional view of pair of anastomosis device components 110, according to one or more embodiments. FIG. 11B is a plan view of the pair of anastomosis device component 110 showing the cross section of the anastomosis devices, according to one or more embodiments.

The second anastomosis device component 110B includes a sensor 1140 configured for light-based measurement of oxygen saturation (SpO2), and a clear window 1145 through which light passes to facilitate SpO2 measurement and a support structure 1155 maintaining the position of the sensor 1140. In addition, the first anastomosis device component 110A includes a first magnetic element 1165 and the second anastomosis device component 110B includes a second magnetic element 1160. The magnetic elements 1160 and 1165 within anastomosis device components may be made of neodymium iron boron. Structural support structure 1155 of the anastomosis device components may be polycarbonate. In some embodiments, the first anastomosis device component 110A and the second anastomosis device component 110B are axisymmetric.

In some embodiments, the first anastomosis device component 110A and the second anastomosis device component 110B are configured to be positioned in two parts of a patient's body (e.g., two parts of the gastrointestinal tract). For instance, in a pediatric patient born with the rare congenital malformation esophageal atresia, the first anastomosis device component 110A is placed in the proximal pouch (which is in communication with the mouth) and the second anastomosis device component 110B is placed in the distal pouch (which is in communication with the stomach). In this example, the first anastomosis device component 110A and the second anastomosis device component 110B may have a diameter around 8 mm.

In other embodiments, the anastomosis device components for use in the small bowel may be between 10 and 18 mm in diameter (including any value falling within that range, and in some cases including values of less than 10 mm or greater than 18 mm). Most typically, the components are less than 12 mm tall (e.g., a range of 1 mm to 11 mm, or a range of 10.5 mm to 11.5 mm), though in some cases the components can be more than 12 mm in height. In some embodiments, the measurements might be different for each component.

Device components for use in the colon may be between 10 and 35 mm in diameter (including any value falling within that range, and in some cases including values of less than 10 mm or greater than 35 mm). Most typically, the components are less than 20 mm tall (e.g., a range of 1 mm to 19 mm or a range of 15.5 mm to 19.5 mm), though in some cases the components can be more than 20 mm in height. In some embodiments, the measurements might be different for each component.

In some embodiments, the first anastomosis device component 110A and the second anastomosis device component 110B includes one or more sensors. An array of force sensors may be distributed across the tissue-contacting face of at least one of the first anastomosis device component 110A and the second anastomosis device component 110B. The array of force sensors can read out values associated with magnitudes of force experienced by intervening tissue from the magnetic field-mediated interaction between the two anastomosis device components. Because magnetic force falls off with distance, force sensors will typically capture lower values where device components are farther apart and higher values where device components are closer together. The array of force sensors may provide a two-dimensional map of the force, which in turn can be the basis for determinations about the relative position of the two anastomosis device components and about the intervening anatomy. For example, force sensor array outputs may be used to determine that a region of fibrotic tissue is causing axial misalignment of the anastomosis device components. This information may be fed into an actuator system that adjusts the positions of the device components with the aim of achieving improved patient outcomes. For example, the device components can be shifted away from the fibrotic tissue. Because compression of fibrotic tissue can be conducive to realizing anatomical changes that are favorable for the patient, actuator systems can act on device components to compress fibrotic tissue. Compression of fibrotic tissue in stricture subsequent to an earlier attempted surgical repair of esophageal atresia can cause the scar tissue to necrose, paving the way for a healthy esophagus. A variety of other sensors—such as accelerometers, gyroscopes, and SpO2 sensors—may be incorporated into the anastomosis device components and used to provide inputs to actuator systems. Actuator systems may be attachments on the ends of endoscopes. Actuator systems may be sophisticated surgical robotic systems, including laparoscopic surgical robots and endoluminal surgical robots. The interface between the actuator system and the sensor systems may include wired and wireless interfaces. Wireless interfaces may use RFID technology or other RF wireless technologies, such as Bluetooth. Powering of sensor systems may be by wireless means, i.e., RFID harvesting or induction, or by wire or by battery.

Digital Surgical Endoscopy Environment (DSEE)

Magnetic compression anastomosis has wide-ranging applications in gastrointestinal diseases, from bypassing obstruction to stricture treatment to bariatric procedures. While endoscopic placement of magnetic anchors is comparably straightforward, fully endoscopic mating of anchor pairs without laparoscopic assistance has remained challenging, in significant part due to the incomplete nature of the information generally available to the endoscopist during the procedure as to the absolute and relative positions of multiple instruments and devices in the complex three-dimensional environment of the abdominal cavity.

A DSEE creates an intuitive, information-rich digital surgical environment for endoscopic procedures (such as endoscopic mating of magnetic anchors). The DSEE displays real-time position and orientation information for multiple instruments and devices as overlays on preoperative imaging. In some embodiments, the DSEE processing engine generates overlays based on one or more reference nodes positioned on bony landmarks.

Figure 12:
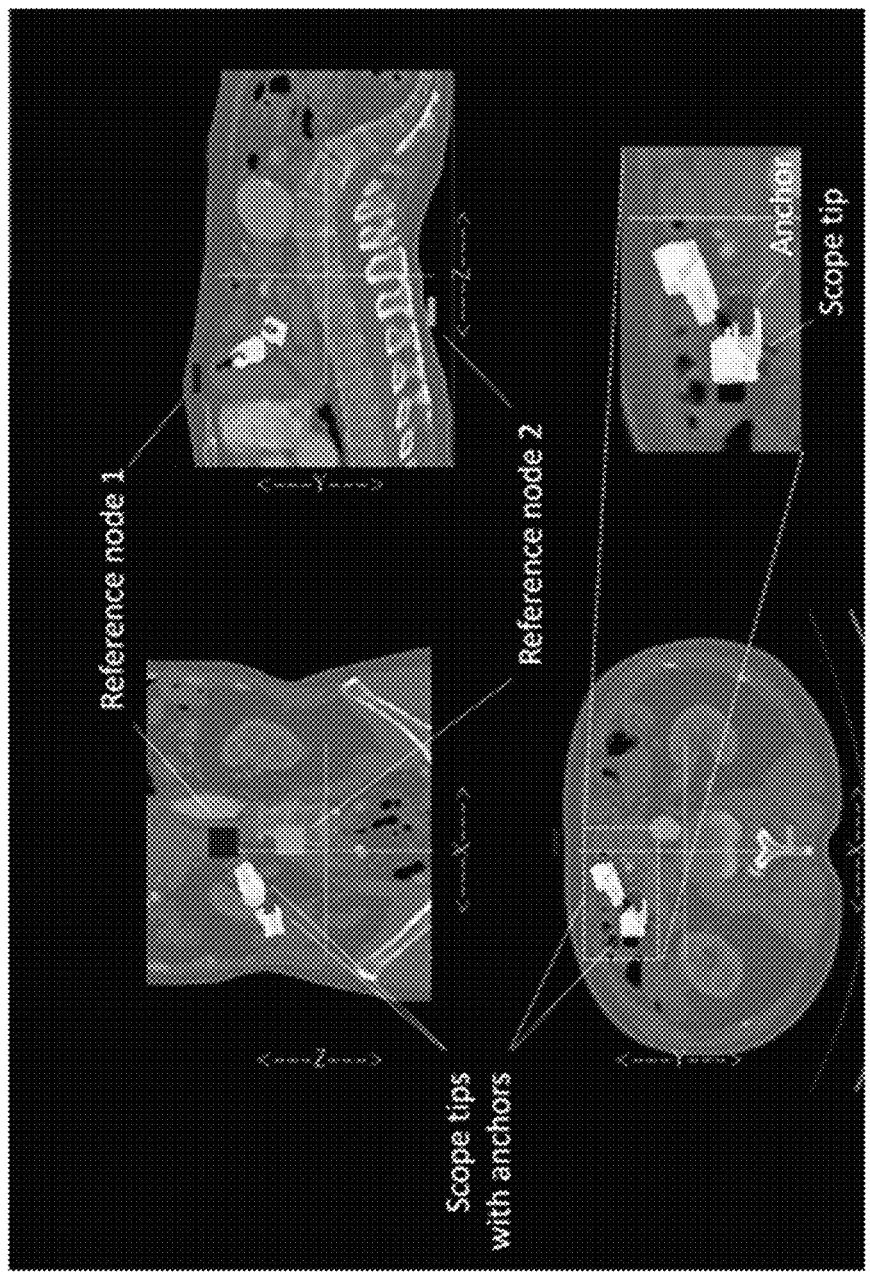
FIG. 12 illustrates a digital surgery environment for magnetic anchor pair mating by dual upper/lower endoscopy, according to one or more embodiments.

FIG. 12 illustrates images generated by the DSEE in cadaveric studies, according to one or more embodiments. The study was conducted using endoscopic magnetic anchor pairing as a test case. The study used an endoscope end cap that accommodates a sensor lead (Polhemus, Colchester, Vt.) and a 15.5 mm magnetic anchor, interfacing with the accessory working channel of the AWC® endoscope system (Ovesco, Tuebingen, Germany). The study made use of dual endoscopes—an Olympus Exera II PCF-H180AL pediatric endoscope and an Olympus CF-HQ190L—each configured with an AWC, sensor lead, anchor, and custom-designed end cap.

As shown in FIG. 12, the DSEE was found to reliably track anchor position and orientation in a working area over a cubic meter in size and with sub-millimeter resolution. The information conveyed by DSEE was found to be a valuable complement to the scope display, providing detailed real-time awareness of anchor position and orientation throughout multiple stages of endoscopy, including the mating of an anchor pair in a simulated dual endoscopy procedure.

Augmented Reality Endoscopic Surgery Systems

Figure 13A:
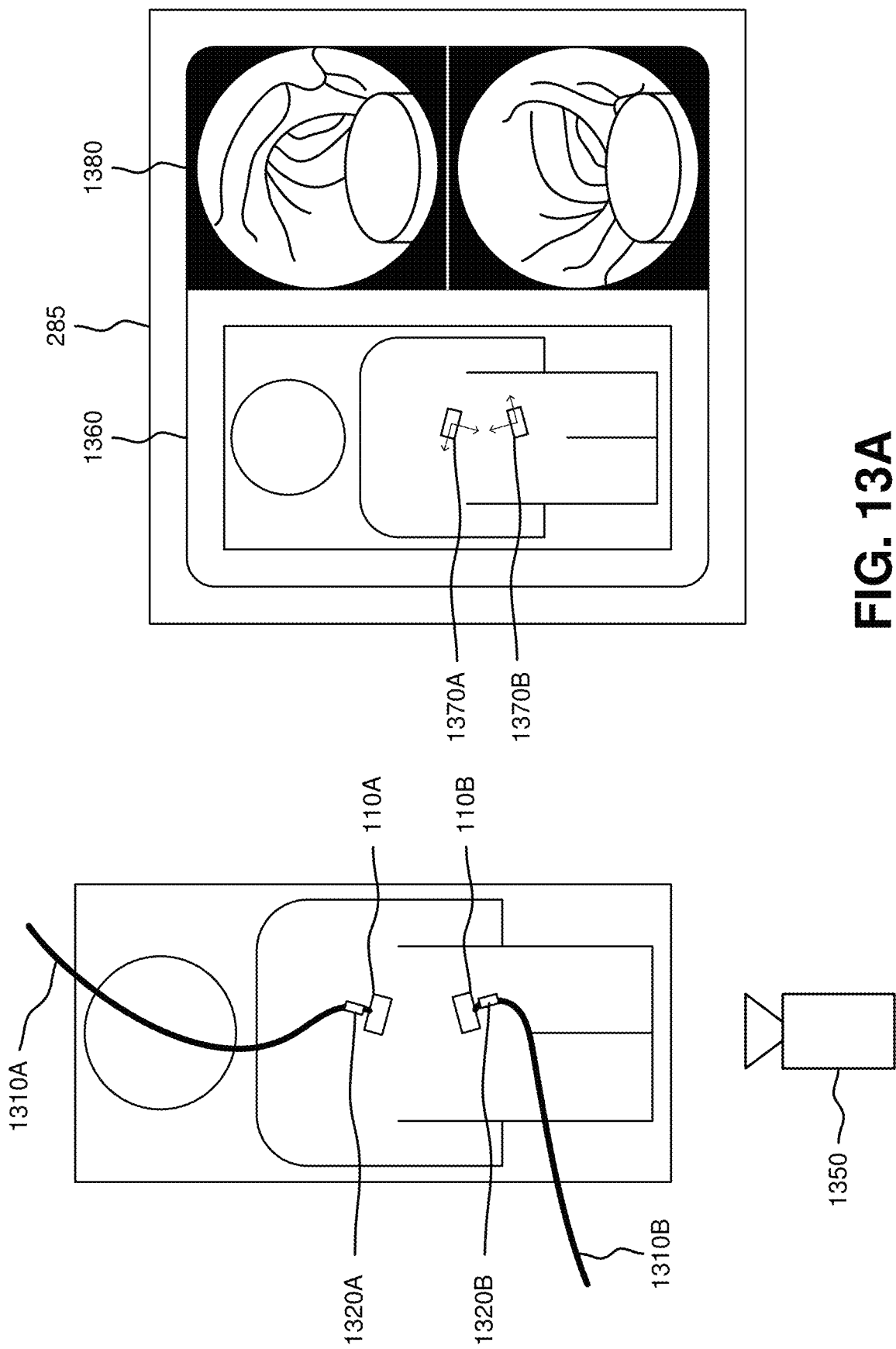
FIG. 13A illustrates an anastomosis system using an augmented reality display conveying information about anastomosis devices based on outputs of sensors, according to one or more embodiments.

FIG. 13A illustrates an anastomosis system using an augmented reality display conveying information about anastomosis devices based on outputs of sensors, according to one or more embodiments.

In some embodiments, the sensor information received from the first anastomosis device component 110A and/or the second anastomosis device component 110B may be combined with additional sensor information to augment the capabilities or accuracy of the anastomosis system. For example, the anastomosis device components 110 may be delivered using endoscopic and/or laparoscopic systems having additional sensors tracking the various components of the endoscopic or laparoscopic systems.

In some embodiments, sensors of the endoscopic system used for delivering the anastomosis device components 110 may facilitate tracking the position and orientation of endoscope tips while an endoscopist manipulates an endoscope. Sensor systems for tracking endoscope tip position, orientation and trajectory can include components affixed on or near the tips of endoscopes that can be precisely located by base stations using tuned electromagnetic fields. Electromagnetic sensing systems can include software and hardware for analyzing position and orientation data for two or more components affixed on or near the tips of two or more endo scopes.

The anastomosis system may analyze the sensor information received from the endoscopic system and the results of the analysis may be presented on a display device (such as a monitor, a head-mounted display device, etc.) or communicated in other ways to endoscopists using the anastomosis system. In some embodiments, the anastomosis system may combine sensor information from the endoscopic system (such as endoscope tip tracking information) with information from imaging systems such as x-ray and ultrasound. Imaging system informational outputs can be real-time informational outputs or informational outputs from an earlier time-point.

In the example of FIG. 13A, a first anastomosis device component 110A is deployed at the tip of a first endoscope 1310A and a second anastomosis device component 110B is deployed at the tip of a second endoscope 1310B. A sensor module 1320A at the tip of the first endoscope 1310A and a sensor module 1320B at the tip of the second endoscope 1310B may provide information, such as information about endoscope tip position and orientation to the anastomosis system. The sensor modules 1320A and 1320B of the endoscopes 1310 may be in communication with the hub 250 of the anastomosis system.

The hub 250 may receive sensor information from the sensor modules 1320 of the endoscopes 1310, and additionally sensor information from the first anastomosis device component 110A and the second anastomosis device component 110B. The hub 250 may combine sensor array information with other patient information, such as the location of anatomic landmarks.

The display 285 can be a monitor or a head-mounted display. The combination of information can be communicated as an augmented reality or mixed reality environment. For example, the anastomosis devices can be depicted as virtual objects superimposed on the field of view of a head-mounted display, such as the HoloLens 2 or other head-mounted display.

The anastomosis system may output information obtained based on the analysis of the sensor information from the sensor modules 1320 of the endoscopes 1310, sensor information from the first anastomosis device component 110A and the second anastomosis device component 110B, and/or additional information such as information received from an imaging system 1350 (such as a camera, an x-ray system, an ultrasound system, a CT scanner, etc.)

In some embodiments, the output provided in the display 285 includes an augmented reality (AR) or virtual reality (VR) feed 1360. The AR (or VR) feed 1360 may superimpose information obtained by analyzing the sensor information from the sensor modules 1320 of the endoscopes 1310 and/or sensor information from the first anastomosis device component 110A and the second anastomosis device component 110B to an image or video received from an imaging system 1350. For example, the AR (or VR) feed 1360 may superimpose markers 1370 (e.g., virtual objects) to a video feed received from an imaging system (such as a camera capturing a video of the patient). The markers 1370 may correspond to the location and orientation of each of the endoscope tips and/or anastomosis device components. For example, the markers 1370 include a first marker 1370A corresponding to the location and orientation of the tip of the first endoscope 1310A, and a second marker 1370B corresponding to the location and orientation of the tip of the second endoscope 1310B. The first marker 1370A may be determined based on sensor information received from the sensor module 1320A of the first endoscope 1310A (and optionally based on sensor information received from the first anastomosis device component 110A). The second marker 1370B may be determined based on sensor information received from the sensor module 1320B of the second endoscope 1310B (and optionally based on sensor information received from the second anastomosis device component 110B).

In some embodiments, the markers 1370 may additionally be determined based on a pose (e.g., location and orientation) of the imaging system 1350. That is, the anastomosis system may determine the position of the first marker 1370A and the second marker 1370B relative to a point of view (POV) of the imaging system 1350. In some embodiments, the imaging system may be associated with a set of sensors that track a position and orientation (or change in position and change in orientation) of the imaging system (such as when the imaging system is embedded in a head mounted display), and the anastomosis system determines where to render the markers 1370 based on the sensor information received from the sensors associated with the imaging system.

In some embodiments, the markers 1370 may visually indicate the orientation of the tip of the endoscopes or the orientation of the anastomosis device components. For instance, the markers 1370 may visually display one or more axes (such as lines or arrows) indicating the orientation of the tip of the endoscopes or the orientation of the anastomosis device components.

Moreover, in some embodiments, the output provided in the display 285 includes one or more video feeds 1380 corresponding to the first endoscope 1310A and the second endoscope 1310B. Alternatively, the display 285 may provide information derived from sensor information received from the first anastomosis device component 110A and the second anastomosis device component 110B (e.g., a distance between the anastomosis device component 110A and the second anastomosis device component 110B, and angle between the anastomosis device component 110A and the second anastomosis device component 110B, etc.).

Figure 13B:
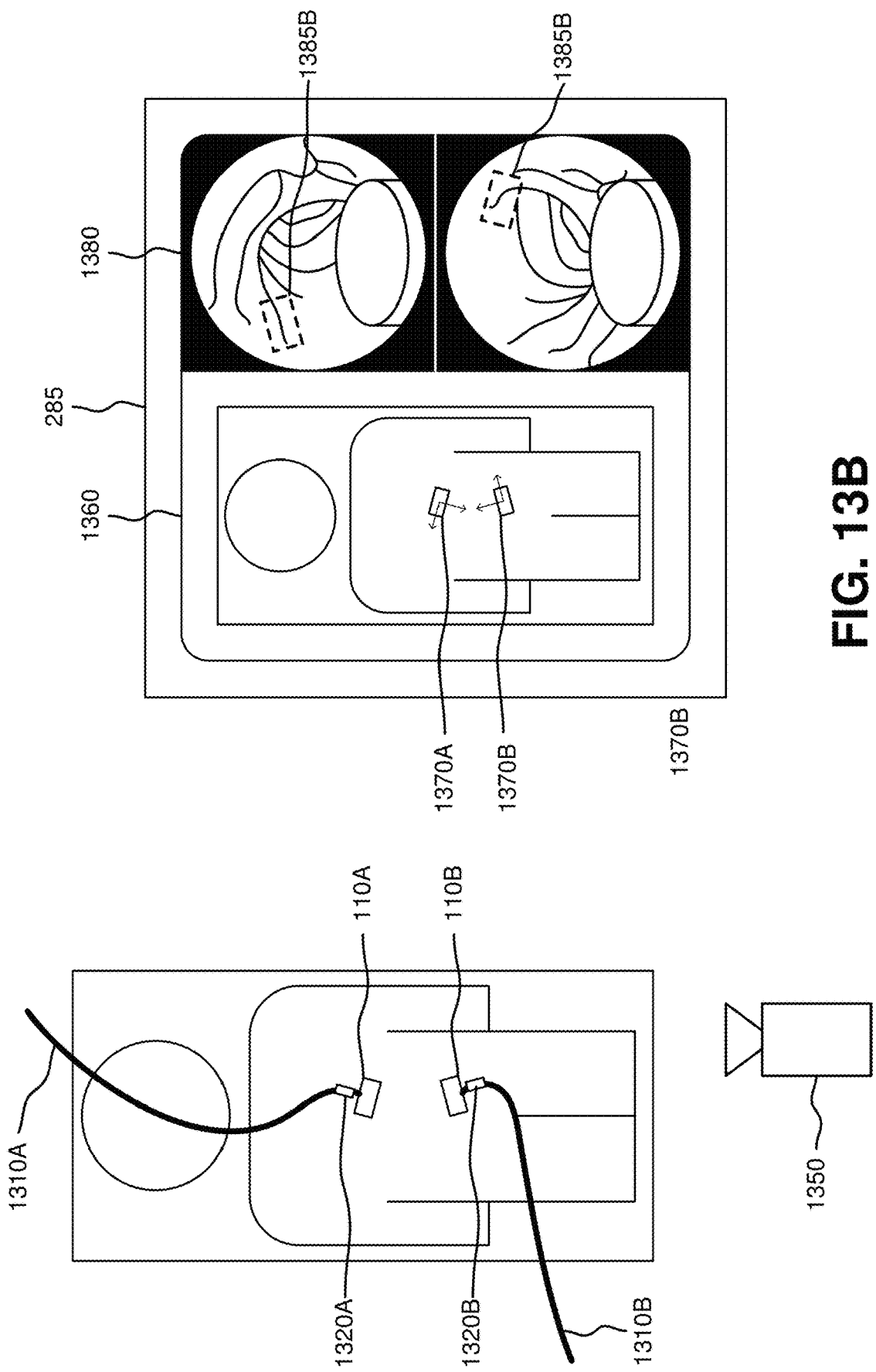
FIG. 13B illustrates an anastomosis system using an augmented reality display conveying information about anastomosis devices based on outputs of sensors, according to other embodiments.

FIG. 13B illustrates an anastomosis system using an augmented reality display conveying information about anastomosis devices based on outputs of sensors, according to other embodiments. As illustrated in FIG. 13B, in some embodiments, the one or more video feeds 1380 corresponding to the first endoscope 1310A and the second endoscope 1310B may display markers 1385 representing anastomosis device components. For example, the video feed corresponding to the first endoscope 1310A can display a marker 1385B providing information about the position and orientation of the second anastomosis device 110B, and the video feed corresponding to the second endoscope 1310B may display a marker 1385A providing information about the position and orientation of the first anastomosis device 110A.

Figure 13C:
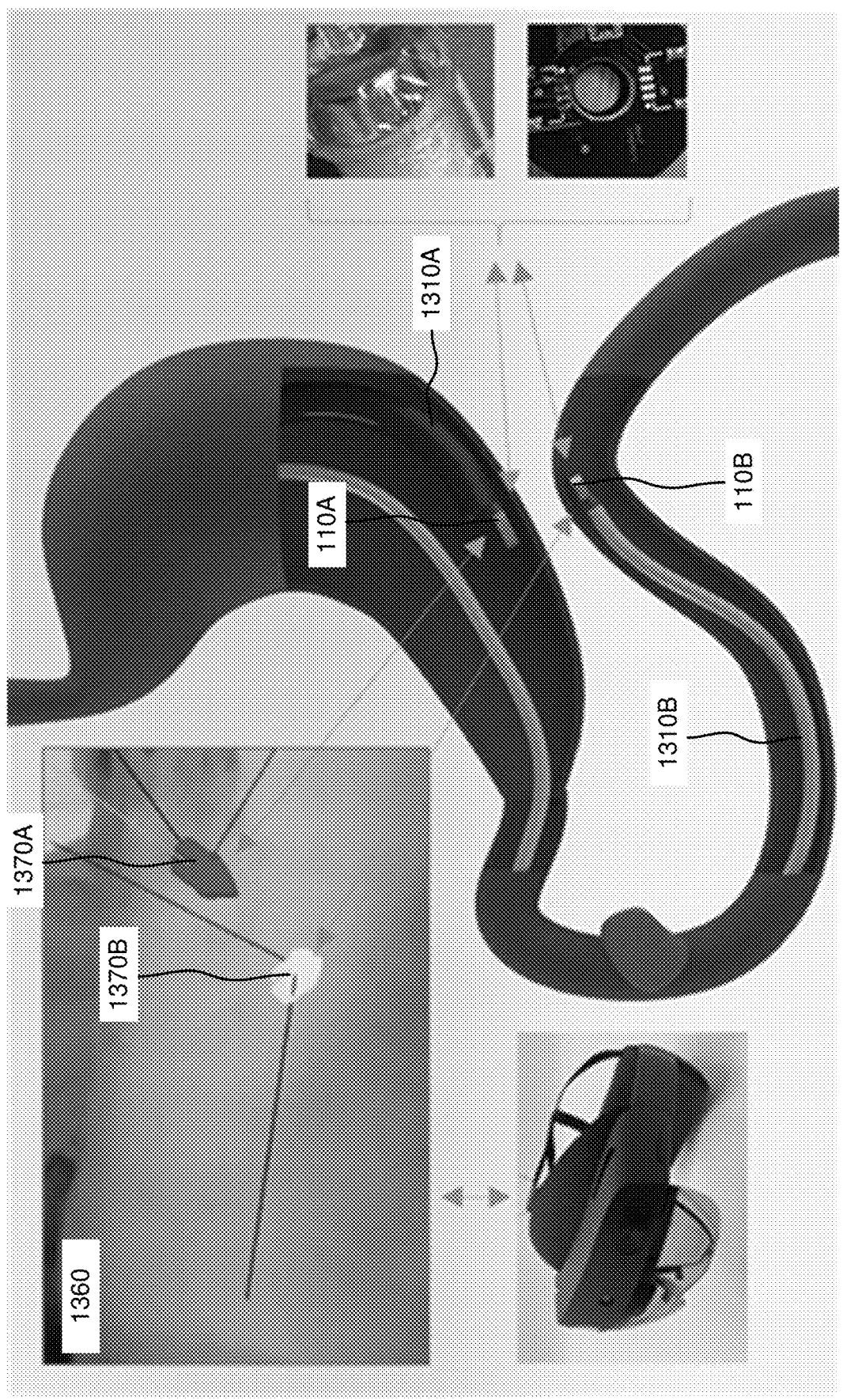
FIG. 13C illustrates an experimental setup of an anastomosis system using an augmented reality display, according to one or more embodiments.

FIG. 13C illustrates an experimental setup of an anastomosis system using an augmented reality display, according to one or more embodiments. The study was conducted using a full-fledged augmented reality dual-scope endoscopy system, where scopes and anastomosis devices are represented as virtual objects superimposed on external anatomy. The system was designed to be user-selectable between an auxiliary display configuration, where the virtual objects are overlaid on a live camera feed of the outside of the patient, and a head-mounted display configuration, where the virtual objects are overlaid in the user's field of view using combiner lenses. The study utilized custom-designed MCA devices deployed by wires passing through the scope working channels, as well as custom-engineered scope caps.

FIG. 13D illustrates images captured from experimental studies performed using the anastomosis system with an augmented reality display, according to one or more embodiments. Specifically, FIG. 13D illustrates still images from a dual endoscopy MCA procedure. In the still images, the upper MCA device component and scope tip are depicted through marker or virtual object 1370B, and the lower MCA device and scope tip are depicted through marker or virtual object 1370A. In FIG. 13D, the markers 1370A and 1370B are overlaid on a real-time video feed to generate a real-time augmented reality video feed. Moreover, the real-time augmented reality video feed may be displayed along with a real-time video feed of the scope camera of the endoscope corresponding to the upper MCA device (upper left image), a real-time video feed of the scope camera of the endoscope corresponding to the lower MCA device (upper right image), or both a real-time video feed of the scope camera of the endoscope corresponding to the upper MCA device and a real-time video feed of the scope camera of the endoscope corresponding to the lower MCA device (lower left image). In some embodiments, the anastomosis system may display additional information such as information received from an imaging system (such as an x-ray system, an ultrasound system, a CT scanner, etc.) (bottom right).

Figure 14:
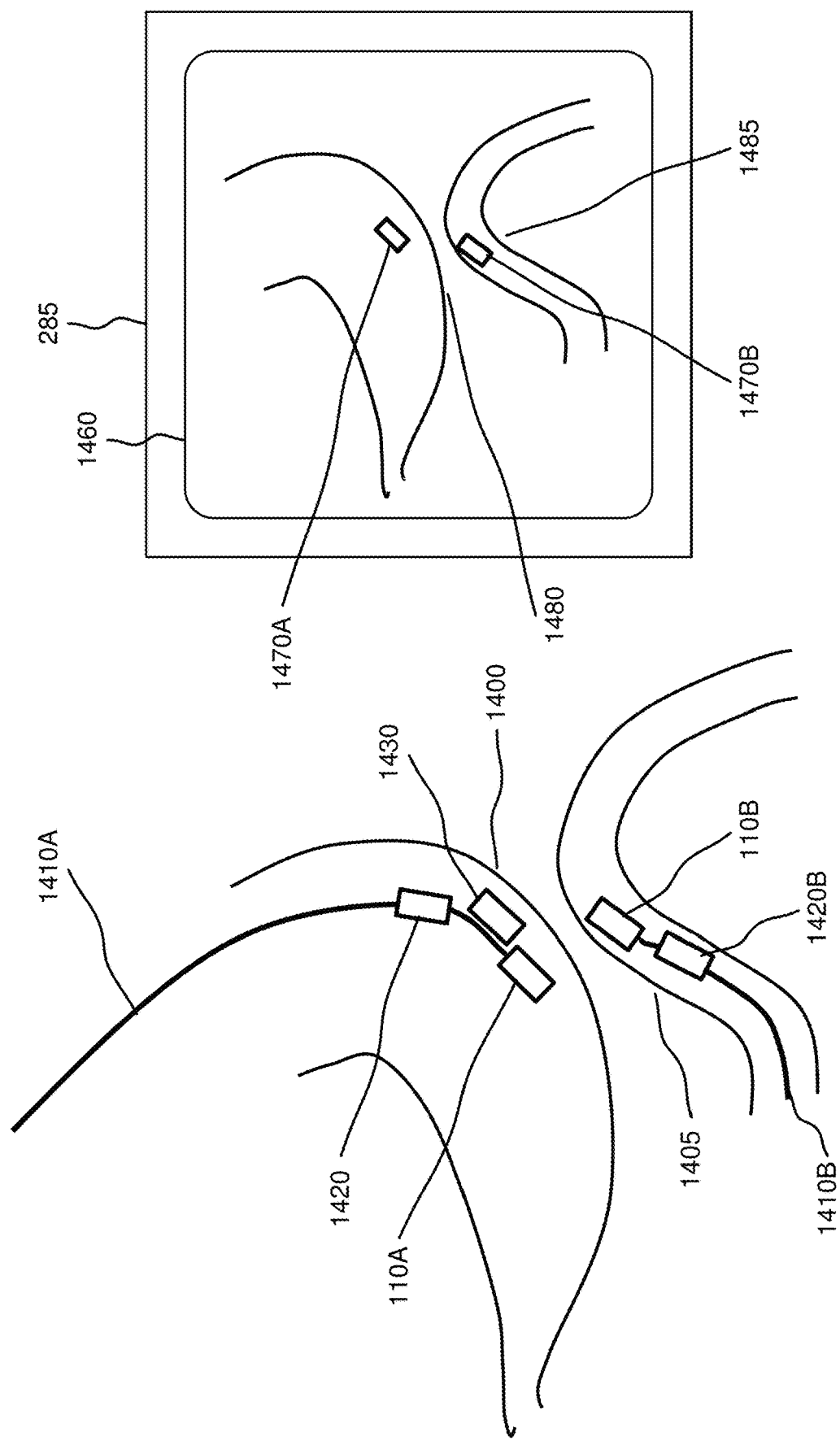
FIG. 14 illustrates a system for endoscopic interventions that includes endoscopic ultrasound.

FIG. 14 illustrates a system for endoscopic interventions that includes endoscopic ultrasound, according to one or more embodiments. In the example of FIG. 14, a first anastomosis device component 110A is deployed at the tip of a first endoscope 1410A and a second anastomosis device component 110B is deployed at the tip of a second endoscope 1410B. A sensor module 1420A at the tip of the first endoscope 1410A and a sensor module 1420B at the tip of the second endoscope 1410B may provide information, such as information about endoscope tip and shaft positions and orientations and about anastomosis device component positions and orientations. The sensor modules 1420A and 1420B may be in communication with the hub 250 of the anastomosis system. In this embodiment, the tip of endoscope 1410A has been advanced into the patient's stomach into close proximity with the mucosa of the greater curvature of the stomach 1400 and the tip of endoscope 1410B has been advanced into the patient's jejunum 1405. An ultrasound module 1430B at the tip of the first endoscope 1410A may provide information about the anatomy. For example, the ultrasound module 1430 can provide information about the distance from the ultrasound module 1430 to each of several locations on the wall of the stomach 1400.

The hub 250 may receive sensor information from the sensor modules 1420 of the endoscopes 1410, and additionally sensor information from the first anastomosis device component 110A and the second anastomosis device component 110B. The hub 250 may combine sensor array information with other patient information, such as the location of anatomic landmarks. The hub 250 may combine sensor array information with information from the ultrasound module 1430.

The display 285 can be a monitor, a head-mounted display, or the like. The combination of information can be communicated as an augmented reality or mixed reality environment. For example, the anastomosis devices can be depicted as virtual objects superimposed on the field of view of a head-mounted display, such as the HoloLens 2 or other head-mounted display.

The anastomosis system may output information obtained based on the analysis of the sensor information from the sensor modules 1320 of the endoscopes 1310, sensor information from the first anastomosis device component 110A and the second anastomosis device component 110B, the ultrasound module 1430, and/or additional information such as information received from an imaging system 1350 (such as a camera, an x-ray system, an ultrasound system, a CT scanner, etc.)

In some embodiments, the output provided in the display 285 includes an augmented reality (AR) or virtual reality (VR) feed 1460. The AR (or VR) feed 1460 may superimpose information obtained by analyzing the sensor information from the sensor modules 1420 of the endoscopes 1410 and/or sensor information from the first anastomosis device component 110A and the second anastomosis device component 110B to a representation of anatomy produced by analysis of the output of the endoscopic ultrasound module 1430. For example, the AR (or VR) feed 1460 may superimpose markers 1470 (e.g., virtual objects) to a representation of the anatomy of the stomach 1480 and the jejunum 1485 produced by analysis of the output of the endoscopic ultrasound module 1430. The analysis of the output of the ultrasound module 1430 may include analysis of the current and historical outputs of the other sensor modules 1420 to improve the accuracy of the representations of the stomach and jejunum. The markers 1470 may correspond to the location and orientation of each of the endoscope tips and/or anastomosis device components. For example, the markers 1470 include a first marker 1470A corresponding to the location and orientation of the tip of the first endoscope 1410A, and a second marker 1470B corresponding to the location and orientation of the tip of the second endoscope 1410B. The first marker 1470A may be determined based on sensor information received from the sensor module 1420A of the first endoscope 1410A (and optionally based on sensor information received from the first anastomosis device component 110A). The second marker 1470B may be determined based on sensor information received from the sensor module 1420B of the second endoscope 1410B (and optionally based on sensor information received from the second anastomosis device component 110B).

In some embodiments, the markers 1470 may visually indicate the orientation of the tip of the endoscopes or the orientation of the anastomosis device components. For instance, the markers 1470 may visually display one or more axes (such as lines or arrows) indicating the orientation of the tip of the endoscopes or the orientation of the anastomosis device components. The markers 1470 may also visually display specific components of the anastomosis device components, such as integrated electrocautery components.

Moreover, in some embodiments, the output provided in the display 285 includes one or more video feeds corresponding to the first endoscope 1410A and the second endoscope 1410B. Alternatively, the display 285 may provide information derived from sensor information received from the first anastomosis device component 110A and the second anastomosis device component 110B (e.g., a distance between the anastomosis device component 110A and the second anastomosis device component 110B, and angle between the anastomosis device component 110A and the second anastomosis device component 110B, etc.).

Figure 15:
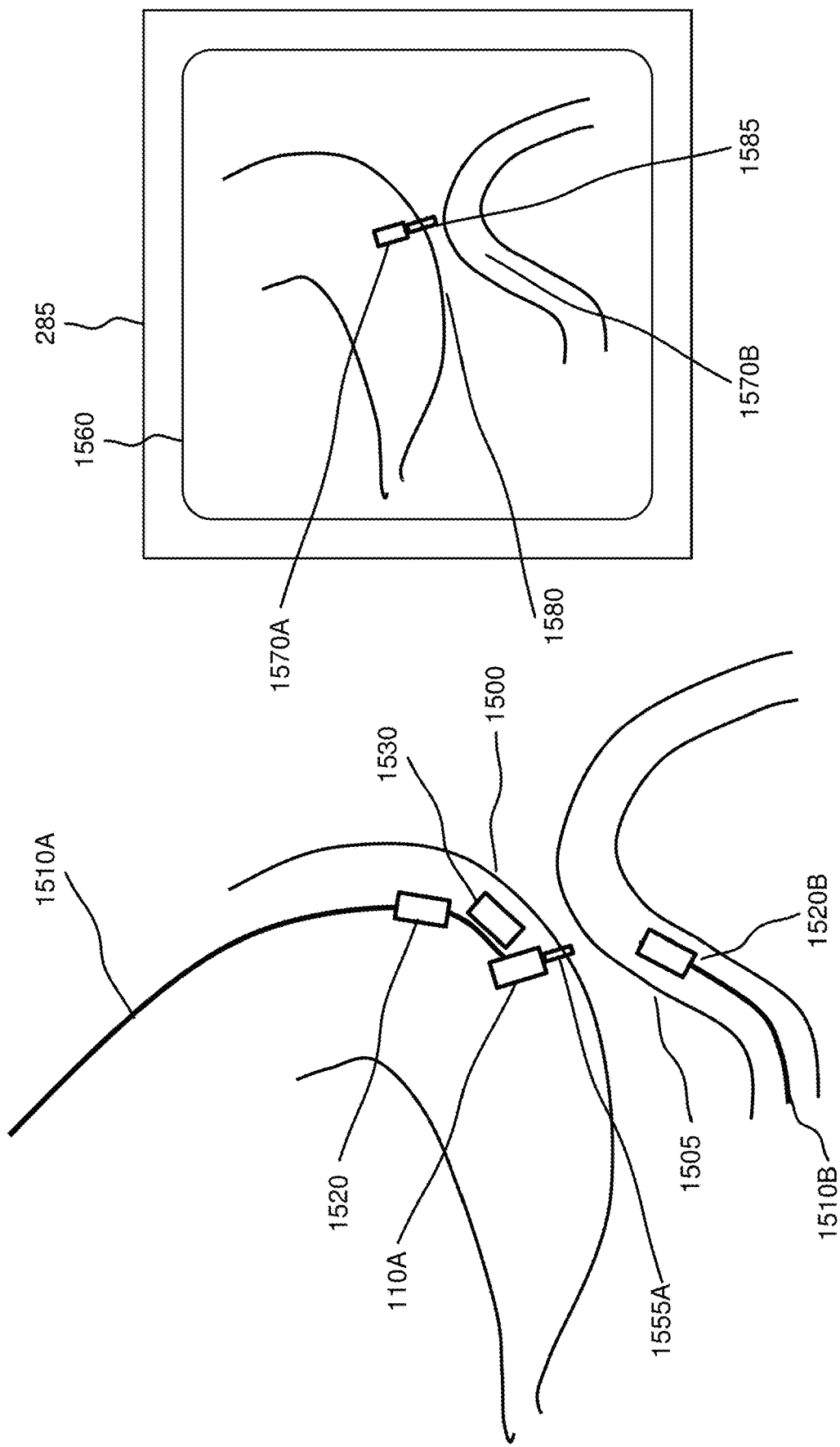
FIG. 15 illustrates a system for endoscopic interventions that includes endoscopic ultrasound and electrocautery.

FIG. 15 illustrates a system for endoscopic interventions that includes endoscopic ultrasound and electrocautery, according to one or more embodiment. In the example of FIG. 15, an anastomosis device component 110A is deployed at the tip of a first endoscope 1510A. A sensor module 1520A at the tip of the first endoscope 1510A and a sensor module 1520B at the tip of a second endoscope 1510B may provide information, such as information about endoscope tip and shaft positions and orientations and about anastomosis device component positions and orientations. The sensor modules 1520A and 1520B may be in communication with the hub 250 of the anastomosis system. In this illustration, the tip of endoscope 1510A has been advanced into the patient's stomach into close proximity with the mucosa of the greater curvature of the stomach 1500 and the tip of the endoscope 1510B has been advanced into the patient's jejunum 1505. An ultrasound module 1530B at the tip of the first endoscope 1510A may provide information about the anatomy. For example, the ultrasound module 1530 can provide information about the distance from the ultrasound module 1530 to each of several locations on the wall of the stomach 1500.

The anastomosis device 110A can include an electrocautery component 1555A. The electrocautery component 1555A can be used to create an opening in the wall of the stomach 1500. The electrocautery component 1555A can be used to create an opening in the wall of the jejunum 1505. A needle or other cutting component can be used to create openings in the walls of the stomach and jejunum. A stent can be deployed through openings in the walls of the stomach and the jejunum. The stent can have flanges or other features to maintain close proximity between the stomach and the jejunum. The activation of the electrocautery component 1555A can be controlled, in whole or in part, by signals output from the hub 250 based on analysis of sensor information from the sensor modules 1520 of the endoscopes 1510, sensor information from the anastomosis device component 110A, the ultrasound module 1530, and/or additional information such as information received from an imaging system (such as a camera, an x-ray system, an ultrasound system, a CT scanner, etc.). The deployment of the stent can be controlled, in whole or in part, by signals output from the hub 250 based on analysis of sensor information from the sensor modules 1520 of the endoscopes 1510, sensor information from the anastomosis device component 110A, the ultrasound module 1530, and/or additional information such as information received from an imaging system (such as a camera, an x-ray system, an ultrasound system, a CT scanner, etc.).

Example Configuration and Use

Considering the example where the system is used for a patient with esophageal atresia, a congenital malformation where there is not communication between the mouth and the stomach, the following steps may be used according to one example implementation. In some embodiments, these steps can occur in different orders than presented here, and there may be more or fewer steps that are described below.

First, the proximal anchor (such as the first anastomosis device component 110A) is placed in the proximal pouch. The system may include a first catheter-like device that the surgeon uses to maneuver the proximal anchor into place.

Next, the distal anchor (such as the second anastomosis device component 110B) is placed in the distal pouch. The system includes a second catheter-like device that the surgeon can use to maneuver the distal anchor into place. The distal anchor may be expandable, to facilitate passage of the distal anchor through the stoma or the esophageal sphincter. For example, the distal anchor may be supplied in a number of pieces that self-assemble after being put up in the distal pouch one at a time.

Next, the anchors are mated. A surgeon can use dedicated tools for mating. A surgeon can use conventional tools for mating, such as a pediatric gastroscope or a bronchoscope. A robotic device can perform mating steps. Sensor systems in the anchors provide information, as described elsewhere. This information may be fed into an actuator system. Thus, using the sensor information, the actuator system may adjust the anchors.

In some embodiments, there may be software or computer code associated with the system, including software for processing certain data relating to or results of the system, e.g., information from or related to sensors, actuators and other components. The software or computer code may be stored on a computer-readable storage medium that when executed by a computer processor cause the processor to perform certain steps based on the stored code. The computer-readable storage medium and/or processor may be on the device components (e.g., magnetic elements) or may be on an external system that performs the analysis, such as a client device (e.g., a laptop, a desktop computer, a mobile phone, a tablet, or other computer system), a server or a collection of servers, a cloud computing platform, among others. In some cases, one or more components of the system communicate and transfer information across wired or wirelessly between them, e.g., over a local network, via Bluetooth, over the internet, etc.

Figure 16:
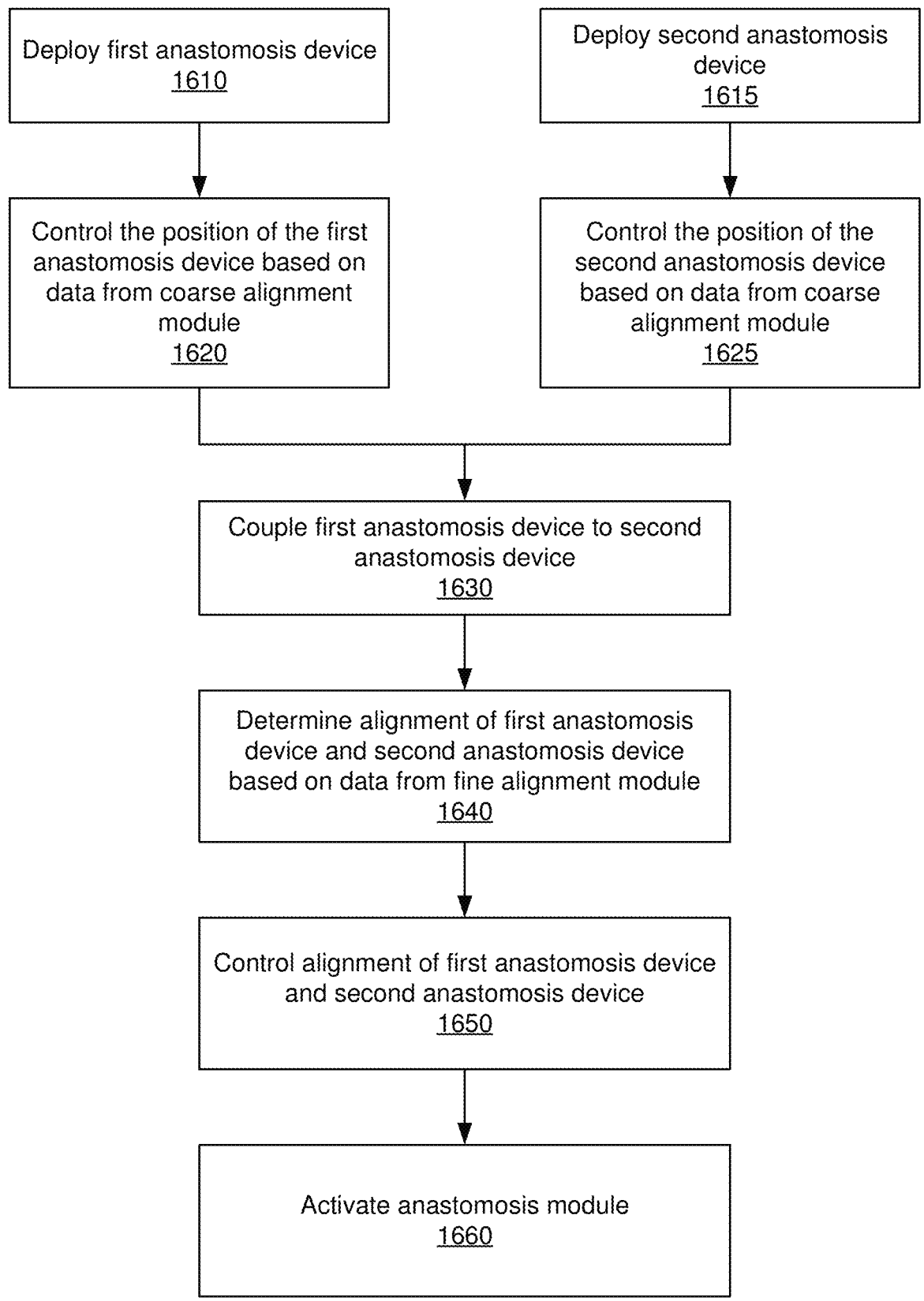
FIG. 16 is flow diagram of a process for creating an anastomosis, according to one or more embodiments.

FIG. 16 is flow diagram of a process for creating an anastomosis, according to one or more embodiments. The first anastomosis device component 110A is deployed 1610 to a first location within the first lumen 120A. For instance, the first anastomosis device component 110A is deployed using a first catheter 275. Similarly, the second anastomosis device component 110B is deployed 1615 to a second location within the second lumen 120B (e.g., using a second catheter 275).

Based on data from the coarse alignment module 220, the position of the first anastomosis device component 110A is controlled 1620. In some embodiments, the position of the first anastomosis device component is controlled based on data from the coarse alignment module 220A embedded in the first anastomosis device component 110A. Alternatively, the position of the first anastomosis device component is controlled based on data from the coarse alignment module 220B embedded in the second anastomosis device component 110B. For example, the catheter used for deploying the first anastomosis device component may be controlled based on data from the coarse alignment module 220A of the first anastomosis device component 110A and/or the coarse alignment module 220B of the second anastomosis device component 110B.

Similarly, based on data from the coarse alignment module 220, the position of the second anastomosis device component 110B is controlled 1625. In some embodiments, the position of the second anastomosis device component is controlled based on data from the coarse alignment module 220B embedded in the second anastomosis device component 110B. Alternatively, the position of the second anastomosis device component is controlled based on data from the coarse alignment module 220A embedded in the first anastomosis device component 110A. For example, the catheter used for deploying the second anastomosis device component may be controlled based on data from the coarse alignment module 220A of the first anastomosis device component 110A and/or the coarse alignment module 220B of the second anastomosis device component 110B.

The first anastomosis device component 110A is coupled 1630 to the second anastomosis device component 110B through the walls of the first lumen 120A and second lumen 120B. In some embodiments, once the first anastomosis device component 110A has engaged with the second anastomosis device component 110B, the fine alignment module 220 is activated. Using data from the fine alignment module 220, an alignment between the first anastomosis device component and the second anastomosis device component is determined 1640. Based on the data from the fine adjustment module 220, the alignment between the first anastomosis device component 110A and the second anastomosis device component 110B is controlled. For example, one or more effectors 270 are controlled to adjust the alignment between the first anastomosis device component 110A and second anastomosis device component 110B.

Once the first anastomosis device component 110A and the second anastomosis device component 110B have been aligned, the anastomosis module 235 is activated to form the anastomosis. For example, the anastomosis module is activated to cut the walls of the first lumen and second lumen, and to fuse the walls of the first lumen and the second lumen together.

Additional Configuration Considerations

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Certain embodiments are described herein as including logic or a number of components, modules, or mechanisms. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A system for forming an anastomosis between a first layer of tissue and a second layer of tissue of a patient's body, the system comprising:
 a first anastomosis device component configured to be delivered to a first lumen inside the patient's body; and
 a second anastomosis device component configured to be delivered to a second lumen inside the patient's body, the second anastomosis device component configured to interact with the first anastomosis device component, the second anastomosis device component comprising:
  one or more sensors configured to capture sensor data for determining an alignment of the second anastomosis device component relative to the first anastomosis device component or for characterizing the position or orientation of the second anastomosis device component in three-dimensional space,
 wherein at least one of the first anastomosis device component and the second anastomosis device component comprises a first mesh or woven structure that can be transitioned between a deployment configuration and a therapeutic configuration, the first mesh or woven structure having at least a flange shape and an adjoining cylindrical region.

2. The system of claim 1, further comprising:
 a controller configured to receive the sensor data captured by the one or more sensors of the second anastomosis device component and configured to determine a distance between the first anastomosis device component and the second anastomosis device component.

3. The system of claim 2, wherein the one or more sensors comprises a first sensor and a second sensor separated by a preset distance, and wherein controller is further configured to determine an angle between the first anastomosis device component and the second anastomosis device component based on sensor data captured by the first sensor and sensor data captured by the second sensor.

4. The system of claim 1, wherein the one or more sensors comprise at least one of an accelerometer, a gyroscope, an ultrasound sensor, and a light-based oxygen sensor.

5. The system of claim 1, wherein the first anastomosis device component comprises one or more magnetic elements, and wherein the second anastomosis device component comprises one or more magnetic elements configured to interact with the one or more magnetic elements of the first anastomosis device component through the first layer of tissue and the second layer of tissue.

6. The system of claim 5, wherein the one or more sensors comprise a force sensor configured to sense a force exerted on the second anastomosis device component due to an interaction between the one or more magnetic elements of the first anastomosis device component and the one or more magnetic elements of the second anastomosis device component.

7. The system of claim 5 wherein the one or more magnetic elements of the first anastomosis device component and the one or more magnetic elements of the second anastomosis device component are selected such that, when the first anastomosis device component and second anastomosis device component are separated by 4 mm, a magnetic force between the first anastomosis device component and second anastomosis device component is between 0.2 Newtons and 20 Newtons.

8. The system of claim 1, wherein the first anastomosis device component comprises a first structure that can be filled with a gas or liquid, and wherein the second anastomosis device component comprises a second structure that can be filled with a gas or liquid.

9. The system of claim 8, wherein at least one of the first structure of the first anastomosis device and the second structure of the second anastomosis device enlarges and becomes rigid upon forcing the gas or liquid into said structure.

10. The system of claim 8, wherein the liquid is saline, and wherein at least one of the first structure and the second structure is made of nylon.

11. The system of claim 1, wherein the first anastomosis device component comprises the first mesh or woven structure that can be transitioned between the deployment configuration and the therapeutic configuration, and wherein the second anastomosis device component comprises a second mesh or woven structure that can be transitioned between a deployment configuration and a therapeutic configuration.

12. A system for forming an anastomosis between a first layer of tissue and a second layer of tissue of a patient's body, the system comprising:
a first anastomosis device component configured to be delivered to a first lumen inside the patient's body; and
a second anastomosis device component configured to be delivered to a second lumen inside the patient's body, the second anastomosis device component configured to interact with the first anastomosis device component, the second anastomosis device component comprising:
one or more sensors configured to capture sensor data for determining an alignment of the second anastomosis device component relative to the first anastomosis device component or for characterizing the position or orientation of the second anastomosis device component in three-dimensional space,
wherein the first anastomosis device component comprises a first mesh or woven structure that can be transitioned between a deployment configuration and a therapeutic configuration, wherein the second anastomosis device component comprises a second mesh or woven structure that can be transitioned between a deployment configuration and a therapeutic configuration, and
wherein in the therapeutic configuration, the first mesh or woven structure has a flange shape, and the second mesh or woven structure has a flange shape and an adjoining cylindrical region.

13. The system of claim 1, further comprising:
one or more effectors for manipulating at least one of the first anastomosis device component and the second anastomosis device component based at least on the sensor data captured by the one or more sensors of the second anastomosis device component.

14. The system of claim 13, wherein the one or more effectors comprise one of an end effector of an endoscopic robotic surgical system and an end effector of a laparoscopic robotic surgical system.

15. The system of claim 1, further comprising:
a first endoscope configured to hold the first anastomosis device component to deliver the first anastomosis device component to the first lumen inside the patient's body, the first endoscope comprising one or more endoscope sensors for determining a position and orientation of a tip of the first endoscope;
a second endoscope configured to hold the second anastomosis device component to deliver the second anastomosis device component to the second lumen inside the patient's body, the second endoscope comprising one or more endoscope sensors for determining a position and orientation of a tip of the second endoscope; and
a display device for displaying configured to display a video feed overlaid with a first marker corresponding to the first endoscope and a second marker corresponding to the second endoscope, wherein a position of the first marker and a position of the second marker are determined based on sensor information captured by the one or more sensors of the first endoscope and the one or more sensors of the second endoscope.

16. A method comprising:
deploying a first anastomosis device component, using a first catheter, to a first location within a first lumen;
deploying a second anastomosis device component, using a second catheter, to a second location within a second lumen;
coupling the first anastomosis device component to the second anastomosis device component, wherein the coupling comprises:
determining a position of the first anastomosis device component based on sensor data from a second set of sensors embedded in the first anastomosis device component,
determining a position of the second anastomosis device component based on sensor data from a first set of sensors embedded in the second anastomosis device component,
controlling the first catheter based on at least one of the determined position of the first anastomosis device component and the determined position of the second anastomosis device component, and
controlling the second catheter based on at least one of the determined position of the first anastomosis device component and the determined position of the second anastomosis device component;
determining, based on the sensor data from the first set of sensors embedded in the second anastomosis device component, an alignment between the first anastomosis device component and the second anastomosis device component; and
manipulating at least one of the first anastomosis device component or the second anastomosis device component using an effector based on the determined alignment between the first anastomosis device component and the second anastomosis device component.

17. The method of claim 16, wherein the first anastomosis device component to the second anastomosis device component are coupled through a wall of the first lumen and a wall of the second lumen.

18. The method of claim 16, wherein determining, based on the sensor data from the first set of sensors embedded in the second anastomosis device component, the alignment between the first anastomosis device component and the second anastomosis device component comprises:
determining a distance between the first anastomosis device component and the second anastomosis device component.

19. The method of claim 16, wherein determining, based on the sensor data from the first set of sensors embedded in the second anastomosis device component, the alignment between the first anastomosis device component and the second anastomosis device component comprises:
determining a first distance between the first anastomosis device component and the second anastomosis device component based on sensor data from a first sensor of the first set of sensors;
determining a second distance between the first anastomosis device component and the second anastomosis device component based on sensor data from a second sensor of the first set of sensors; and
determining an angle between the first anastomosis device component and the second anastomosis device component based on the determined first distance and second distance.

20. The method of claim 16, wherein the first set of sensors comprises a force sensor configured to sense a force exerted on the second anastomosis device component due to an interaction between the one or more magnetic elements of the first anastomosis device component and the one or more magnetic elements of the second anastomosis device component.

21. The method of claim 16, wherein the first set of sensors comprises at least one of an accelerometer, a gyroscope, an ultrasound sensor, and a light-based oxygen sensor.

22. The method of claim 16, wherein manipulating at least one of the first anastomosis device component or the second anastomosis device component using an effector based on the determined alignment between the first anastomosis device component and the second anastomosis device component comprises:
controlling one or more effectors based at least on the sensor data captured by the first set of sensors of the second anastomosis device component.

23. The method of claim 22, wherein the one or more effectors comprise one of an end effector of an endoscopic robotic surgical system and an end effector of a laparoscopic robotic surgical system.

24. A system for anastomosis creation, comprising:
a first anastomosis device component configured to be delivered to a first lumen inside a patient's body;
a second anastomosis device component configured to be delivered to a second lumen inside the patient's body;
one or more sensors configured to capture sensor data for determining an alignment of the second anastomosis device component relative to the first anastomosis device component, or determining a position and orientation of the first anastomosis device component and the second anastomosis device component; and
a display for displaying information derived from the sensor data captured by the one or more sensors,
wherein at least one of the first anastomosis device component and the second anastomosis device component comprises a first mesh or woven structure that can be transitioned between a deployment configuration and a therapeutic configuration, the first mesh or woven structure having at least a flange shape and an adjoining cylindrical region.

25. The system of claim 24, wherein the display is a head-mounted display.

26. The system of claim 24, the display is configured to display a location of the first anastomosis device component and a location of the second anastomosis device component as virtual objects overlaid on an image or video feed of the patient's body.

27. The system of claim 24, wherein at least one of the first anastomosis device component and the second anastomosis device component has a tissue-contacting face that is approximately circular with a diameter between 1 mm and 50 mm.

28. A system for anastomosis creation, comprising:
a first device component configured to be delivered to a first lumen inside a patient's body and configured to create an anastomosis;
a second device component configured to be delivered to a second lumen inside the patient's body;
one or more sensors configured to capture sensor data for determining an alignment of the second device component relative to the first device component, or determining a position and orientation of the first device component and the second device component; and
a display for displaying information derived from the sensor data captured by the one or more sensors,
wherein at least one of the first anastomosis device component and the second anastomosis device component comprises a first mesh or woven structure that can be transitioned between a deployment configuration and a therapeutic configuration, the first mesh or woven structure having at least a flange shape and an adjoining cylindrical region.

29. The system of claim 28, wherein the first device component includes one of an electrocautery means and a stent.

30. The system of claim 1, wherein the first mesh or woven structure has a dual-flange shape.

31. The system of claim 1, further comprising a first electromagnetic (EM) sensor on the first anastomosis device component for tracking a position of the first anastomosis device component, a second electromagnetic (EM) sensor on the second anastomosis device component for tracking a position of the second anastomosis device component, and an imaging sensor on the second anastomosis device component for imaging at least a part of the patient's body.

32. The system of claim 24, further comprising a first electromagnetic (EM) sensor on the first anastomosis device component for tracking a position of the first anastomosis device component, a second electromagnetic (EM) sensor on the second anastomosis device component for tracking a position of the second anastomosis device component, and an imaging sensor on the second anastomosis device component for imaging at least a part of the patient's body.

33. The system of claim 28, further comprising a first electromagnetic (EM) sensor on the first anastomosis device component for tracking a position of the first anastomosis device component, a second electromagnetic (EM) sensor on the second anastomosis device component for tracking a position of the second anastomosis device component, and an imaging sensor on the second anastomosis device component for imaging at least a part of the patient's body.

* * * * *